US006650357B1

(12) United States Patent
Richardson

(10) Patent No.: US 6,650,357 B1
(45) Date of Patent: Nov. 18, 2003

(54) COLOR TRANSLATING UV MICROSCOPE

(75) Inventor: Timothy M. Richardson, Bolton (CA)

(73) Assignee: Richardson Technologies, Inc., Ontario (CA)

( * ) Notice: Subject to any disclaimer, the term of this patent is extended or adjusted under 35 U.S.C. 154(b) by 0 days.

(21) Appl. No.: 09/402,467

(22) PCT Filed: Apr. 9, 1998

(86) PCT No.: PCT/CA98/00350

§ 371 (c)(1),
(2), (4) Date: Dec. 23, 1999

(87) PCT Pub. No.: WO98/45744

PCT Pub. Date: Oct. 15, 1998

Related U.S. Application Data

(60) Provisional application No. 60/044,247, filed on Apr. 23, 1997, and provisional application No. 60/041,855, filed on Apr. 9, 1997.

(51) Int. Cl.⁷ .................................. H04N 7/18
(52) U.S. Cl. ........................................ 348/80
(58) Field of Search .............................. 348/80, 61, 29, 348/599; 359/350–353

(56) References Cited

U.S. PATENT DOCUMENTS

| 3,124,682 A | * 3/1964 | Kojima et al. ......... 250/214 VT |
| 4,115,802 A | 9/1978 | Kramer et al. |
| 4,751,571 A | * 6/1988 | Lillquist ..................... 250/330 |
| 4,786,155 A | * 11/1988 | Fantone et al. ............... 348/79 |
| 4,791,310 A | * 12/1988 | Honig et al. ............. 250/458.1 |
| 4,835,704 A | 5/1989 | Eichelberger et al. |
| 5,034,903 A | 7/1991 | Alfano et al. |
| 5,149,972 A | 9/1992 | Fay et al. |
| 5,233,197 A | 8/1993 | Bowman et al. |
| 5,247,340 A | 9/1993 | Ogino |
| 5,260,578 A | * 11/1993 | Bliton et al. ............. 250/461.1 |
| 5,394,268 A | 2/1995 | Lanni et al. |
| 5,398,055 A | 3/1995 | Nonomura et al. |
| 5,481,401 A | * 1/1996 | Kita et al. .................. 359/353 |
| 5,801,881 A | 9/1998 | Lanni et al. |
| 5,802,222 A | * 9/1998 | Rasch et al. .................... 385/1 |

FOREIGN PATENT DOCUMENTS

JP 61 189515 A 8/1986

OTHER PUBLICATIONS

Patent Abstract of Japan, vol. 011, No. 015 (P–536), Jan. 16, 1987.

Zworykin et al., "Ultraviolet Television Color–Tranlsating Microscope," Science, vol. 126, No. 3278, Oct. 25, 1987, pp. 805–810.

* cited by examiner

*Primary Examiner*—Vu Le
(74) *Attorney, Agent, or Firm*—Banner & Witcoff, Ltd.

(57) ABSTRACT

A color translating UV or IR microscope for imaging living or dynamic samples in real time. The microscope includes a UV or IR light source and a first filter for cyclically separating light from the light source into spectral components which illuminate the sample. A device such as an image intensifier converts light received from the sample to visible polychromatic light, e.g., an intensified white light. A second filter set separates the visible polychromatic light into color planes. The first and second filter sets are synchronized with each other so as to enable the color planes to be recombined into a visible multicolor image, wherein each color plane represents illumination of the sample by non-visible light of different wavelengths.

27 Claims, 15 Drawing Sheets

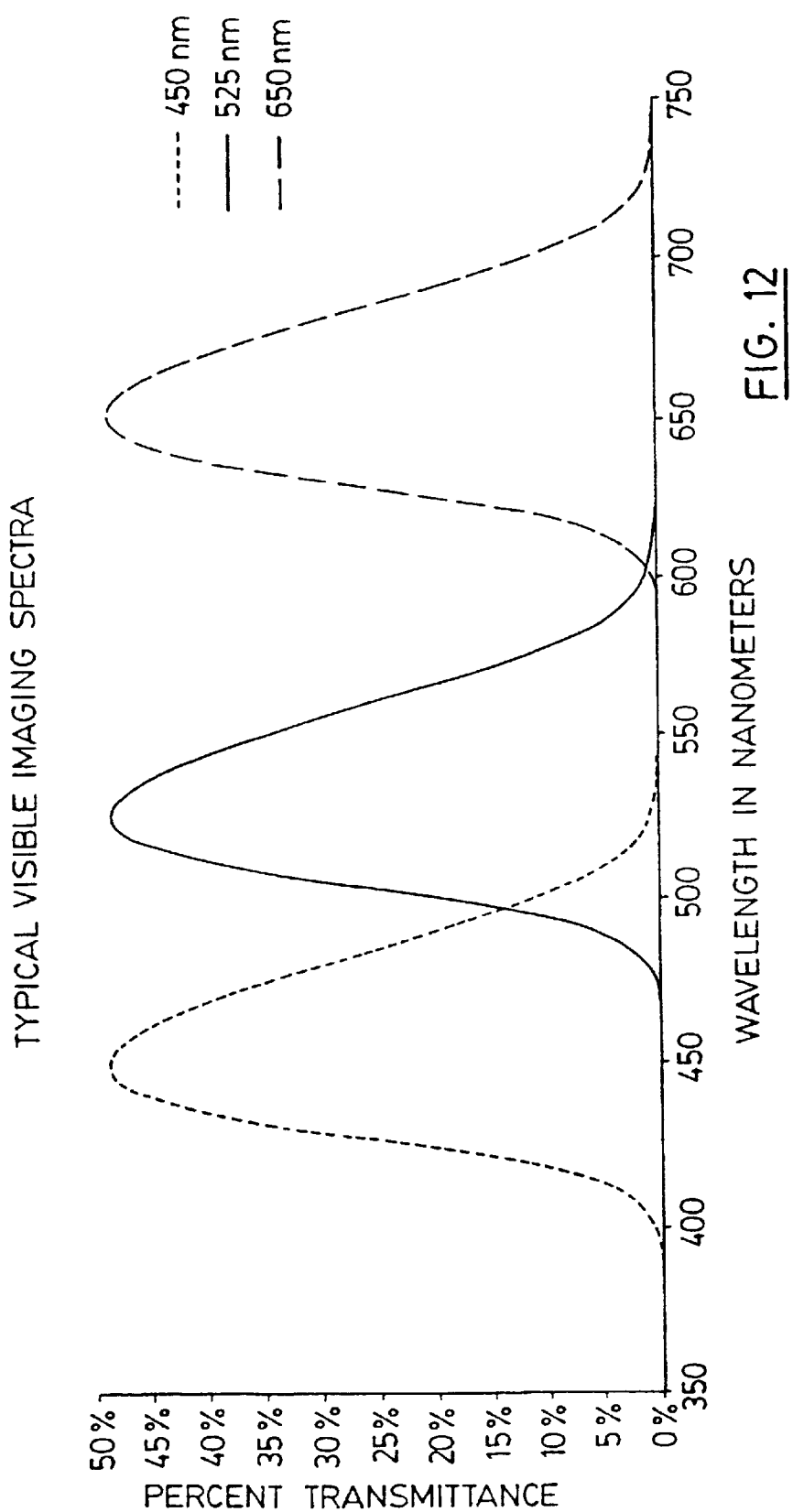

COLOR TRANSLATING UV MICROSCOPE

This application claims the benefit of Provisional application Ser. No. 60/044,247, filed Apr. 23, 1997, and Ser. No. 60/041,855 filed Apr. 9, 1987.

FIELD OF THE INVENTION

The present invention relates to a color translating microscope employing ultraviolet light in place of or in addition to visible and/or infrared light sources. More specifically, the present invention relates to a method and a microscope which determine and represent differential absorption, transmission, reflection, fluorescent and/or Raman characteristics of a sample as a color image to a user.

BACKGROUND OF THE INVENTION

It has been desired for some time to find a low cost, reliable and yet flexible means to view living and/or dynamic processes at high resolution in real time. Another desire is to be able to carry out wide ranging spectral imaging based on differential spectral absorption after such as, Caspersson, T., 1940, "Methods for the determination of the absorption spectra of cell structures", Journal of the Royal Microscopical Society, 60, 8–25, to study biological samples without the addition of any contrast media. Yet another desire is to substantially reduce the amount of light that can potentially damage or affect the behaviour of a sample. In other words, the desire has been to view a sample with the slightest possible interference with its normal behaviour in order to see its operation in a state substantially the same as that which it would normally experience in its usual environment. Accordingly, it has been desired to eliminate stains, fluorochromes, dyes, fixatives, preservatives or other additives and to minimize external fields and radiations such as magnetic, electrical or photon energy.

Color translating UV microscopes are known. In the past many inventors have attempted to produce color translating UV microscopes. For example, some prior art microscopes have used photographic techniques as described in: Barnard, J. E., 1919, "The limitations of microscopy", Journal of the Royal Microscopical Society, 39, 1–13; Martin, L. C., Johnson. 1928, B. K., "UV Microscopy", parts 1 & 2, Journal of Scientific Instruments, 5, 337–344 and 380–387; Lucas, F. F., 1930, "The architecture of living cells", Proceedings of the National Academy of Sciences, 16, 599–607; Barnard, J. E., 1939, "Towards the smallest living things", Journal of the Royal Microscopical Society, 59, 1–10; Brumberg, E. M., 1946, "A microscope for visual colour microscopy in the ultraviolet rays", Comptes Rendus (Doklady) de I'Academie des Sciences de I'URSS, 52:6, 499–502; and Land, E. H., et al, 1949, "A colour translating UV microscope", Science, 109, 371–374. The contents of these publications are incorporated herein by reference.

Other prior art attempts at color translating UV microscopes have been made using video techniques as described in: Zworykin, V. K., Hatke, F. L., 1957, "Ultraviolet television colour translating microscope", Science, 126, 805–810; Zworykin, V. K., Berkley, C., 1962, "Ultraviolet colour translating television microscopy", Annals of the New York Academy of Science, 97, 364–379; Caspersson, T., 1964, "The ultraviolet microscope", Journal of the Royal Microscopical Society, 83, 67–68; and Caspersson, T., 1964, "The study of living cells with the ultraviolet microscope", Journal of the Royal Microscopical Society, 83, 95–96. The contents of these publications are incorporated herein by reference.

It is believed that all these prior art attempts failed due to the complex nature of the solutions attempted, the attendant costs and the high operating and maintenance burden and costs. The results from these systems were mediocre at best due to the delay in image availability in the photographic processes and due to the low resolution and long integration times of the video solutions available at the time the work was carried out.

A more recent attempt at a useful UV microscope is shown in U.S. Pat. No. 5,481,401 to Kita et al., the contents of which are incorporated herein by reference. As shown in FIG. 9 of this reference, a final image is produced from the combination of a monochromatic UV microscope image with a color visible light image to obtain a pseudo color image. In other embodiments taught by the reference, separate displays of the monochromatic UV image and the color visible light image are provided to the user. This reference suffers from disadvantages in that, for example, it needs high power UV illumination to provide sufficient illumination to the UV video camera which will be detrimental to the sample, it does not combine multiple three UV images from the same camera created with successive selections of light of different wavelength center and bandpass to create a full three colour visible image and therefore it is prone to misalignment of the individual cameras, and it is preset and not rapidly adjustable as to the wavelengths of light chosen for imaging, it does not use the extending resolving power of the deep UV range of the spectrum in which cellular absorption of biological specimens begins to offer the advantages of absorption staining of living systems and it will not resolve images at resolutions greater than those possible under visible light viewing conditions, as the final displayed visible light and monochromatic UV images are presented to the user at the same pixel resolution.

It is desired to have a color translating UV microscope which provides substantially real time image presentation without damage to the sample and which ranges from the relatively simple to construct and to use simple version to the powerful and comprehensive imaging system in the research version described herein.

SUMMARY OF THE INVENTION

It is an object of the present invention to provide a novel color translating UV microscope which obviates or mitigates at least one disadvantage of the prior art.

According to a first aspect of the present invention, there is provided a microscope for translating spectral information to a visible color image in which light from a source is separated into components by either a set of two or more filters or a device for providing wavelength limited light and then passed through or reflected off the sample and then imaged by an objective lens onto a video camera where it is converted to visible light by a fluorescent coating on the photosensitive surface of video camera which provides the image as an electronic signal which is then converted into electronic data by a video to computer interface system and then recombined into a multicolor image by computer processing finally creating a color visible image on a display monitor where the computer is supplied with information on the position of the filters or wavelength limited light in order to synchronize acquisition of the images and the color translation and recombination process.

According to another aspect of the present invention, there is provided a microscope for translating spectral information to a visible color image in which light from one or more sources is separated into components by either a set of two or more filters or device for providing wavelength limited light and then passed through or reflected off an sample then imaged onto the input of an image intensifier by an objective lens then converted to visible light by the image intensifier or other wavelength translating device the output of which is then imaged on the input of a video camera which provides the image as an electronic signal which is then converted into electronic data by a video to computer interface system and then recombined into a multicolor image by computer processing finally creating a color visible image on a display monitor where the computer is supplied with information on the position of the filters or wavelength limited light in order to synchronize acquisition of the images and the color translation and recombination process.

According to yet another aspect of the present invention, there is provided a microscope for translating spectral information to a visible color image in which light from a source which emits narrow spectral lines, as opposed to a continuum of spectra, is separated into components after passing through a sample and is then converted to visible polychromatic light by a converter such as an image intensifier and is then recombined into a multicolor image by a combining images captured by a video camera, video interface and computer where such images are synchronized with the filter system.

According to yet another aspect of the present invention, there is provided an optical microscope system where an image intensifier and CCD camera combined with a computerized image capture and image processing system is used to convert images collected in wavelengths outside the normal range of human vision, such as soft x-ray, UV or IR, to visible images and where, while at least one of the images collected is in the range 200 nanometers to 300 nanometers, some of the other images used to produce the final color image can be collected in the range from 300 to 3300 nanometers.

According to yet another aspect of the present invention, there is provided a microscope which includes active optical feedback for stabilization of the position and intensity of the illuminating optical system.

According to yet another aspect of the present invention, there is provided a microscope which includes active optical monitoring for recording and providing the data to allow relating the effects of the dosage of the illuminating radiation to the observed effects in the samples and for modulation of that illumination to prolong sample life.

According to yet another aspect of the present invention, there is provided a microscope that is capable of selecting between brightfield, darkfield, and reflected brightfield or reflected darkfield illumination or phase contrast or other standard forms of illumination under computer control.

According to yet another aspect of the present invention, there is provided a microscope that is capable of switching objective lenses under computer control.

According to yet another aspect of the present invention, there is provided a microscope that is capable of switching image intensifiers under computer control.

According to yet another aspect of the present invention, there is provided a microscope that is capable of switching video cameras under computer control.

It is an object of yet another embodiment of the present invention to provide a novel color translating microscope which obviates or mitigates at least one of the difficulties of the prior art. It is a further object to provide a novel method of forming a color image of the differential absorption of a microscope sample.

According to yet another aspect of the present invention, there is provided a microscope for translating spectral information to a visible colour image in which light from a source is separated into components by a set of two or more filters then passed through an sample then converted to visible polychromatic light by a converter such as an image intensifier and then recombined into a multicolour image by a set of two or more filters where such filter sets are synchronized with each other.

According to yet another aspect of the present invention, there is provided a method of producing an image representing the differential absorption of light by a sample, comprising the steps of:

(i) illuminating a sample with light of a first desired wavelength by imposing an illumination filter between a multiwavelength light source and the sample;

(ii) receiving light from the sample at a photon gain device which converts the received light to an intensified white light;

(iii) filtering said intensified white light with an image filter to obtain visible light at preselected wavelength for said desired wavelength;

(iv) forming an image of said filtered intensified white light; and (v) synchronously changing said illumination filter and said image filter and repeating steps (i) through (iv) to illuminate said sample with light of a second desired wavelength and to form an image from visible light obtained from said intensified white light at a second preselected wavelength for said second desired wavelength.

BRIEF DESCRIPTION OF THE DRAWINGS

Preferred embodiments of the present invention will now be described, by way of example only, with reference to the attached Figures, wherein:

FIG. 12 shows a graph of atypical visible light imaging filter spectra;

DETAILED DESCRIPTION OF THE INVENTION

Figure 1:
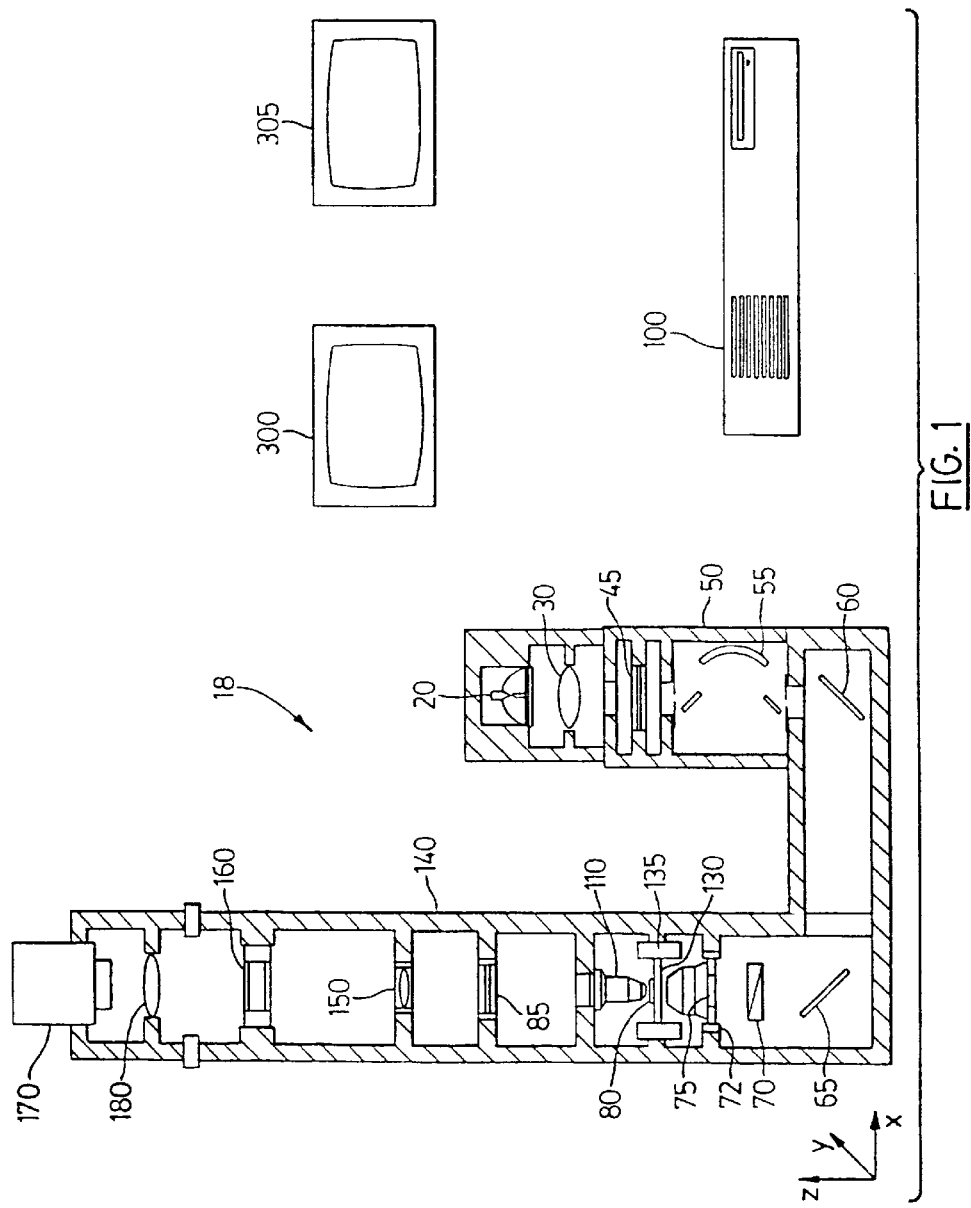
FIG. 1 shows a color translating UV microscope in accordance with an embodiment of the present invention.

This invention stems from the desire to provide a powerful new research and clinical tool which advances the state of the art in microscopes for living or dynamic sample microscopy while maintaining the sample in a state as close as possible to it's normal conditions. In the discussion below, the following abbreviations are employed with these definitions: UV—light from the spectral region of wavelengths shorter than four hundred nanometers; visible—light from the spectral region from four hundred to seven hundred nanometers; IR—light from infrared, the spectral region of wavelengths longer than seven hundred nanometers; NIR—light from near infrared, the spectral region from seven hundred to three thousand three hundred nanometers; and a subset of IR and DIC—differential interference contrast, a means of enhancing image contrast in microscopy. The terms sample denotes the particular thing being imaged by the microscope and normally placed on a slide in a stage or holder in the microscope, it is sometimes referred to in the literature as the object.

Generally, it is desired to carry out wide ranging spectral imaging based on differential spectral absorptions after the work of Caspersson, mentioned above, in order to study biological samples without the addition of any contrast media. It is also desired to follow the movement of highly active or dynamic samples as they move in three dimensional space without a requirement for manual control so that an operator can find a sample component of interest and return some time later and observe where that component has moved to. It is also desired to substantially reduce the amount of light and/or other fields or energy sources that might damage to which the specimen is subjected are reduced. Also, it is desired that the system be relatively easy to set up, use and maintain, while being affordable.

Throughout this patent the microscope along with the related system components are collectively referred to as the UVM. This system will also excel in many other fields of microscopy such as metallographic, crystallographic, forensic and chemical microscopy due to the common requirements of those fields with the field of living microscopy in that chemical spectrophotometric and optical information is important to better characterize and understand the sample. This new microscope system can provide high light microscope resolution, real time high speed image formation for stopping fast action, non-invasive spectral absorption image contrast formation, optical sectioning for three dimensional analysis, and high speed tracking of moving samples or components of samples in three space.

This system employs one or more supervisory and image processing computers which control all the selections, operating levels and wavelengths and modes of the various components of the UVM, and process the image data collected and assemble it into a final image according to a set of operator selected algorithms, and feedback systems from the image data to the control drives of the UVM components to optimize image formation and track living or dynamic samples over time. Without the integration of image processing and machine control made possible by current computer technology, the sophisticated ability of this UVM to form composite images and track living or dynamic samples would not be possible.

This system can produce unique images by rapidly cycling not only the wavelength, bandwidth, polarity and intensity of the illuminating light but also the method of illumination between transmitted brightfield, transmitted darkfield, reflected brightfield, reflected darkfield, phase contrast, and slit ultramicroscopic, as well as being able to rapidly change the polarity and spectral bandwidth, by using filtering or monochromators, of the light emitted from the sample, and change the gain of the image intensifiers to suit the intensity of the resulting light from the sample. These rapid switching functions of the light influencing components is then coupled with the computer's capability to mathematically process the images and carry out numerical operations to add, subtract, multiply, divide or take other mathematical or boolean functions of the data to create the three color output planes seen as red, green and blue on the video display monitor.

An example of the unique capability of this system is the creation of a final image in which structural information obtained in the mid UVC spectrum is shown in blue while fluorescent information excited in the two hundred and fifty nanometer range and emitted in the blue visible spectrum is shown as green and fluorescent information excited in the three hundred and sixty five nanometer range and emitted in the red visible spectrum is subtracted from the green image and the blue image and the result is shown as red. The rapidity of the moving light and light path selecting components of the UVM can be fast enough to produce a full color translated image of a moving sample in real time. This requires ninety image planes per second for a thirty frame per second final color image. The image processor must be able to handle mathematical operations on ninety frames per second, output the result of these operations to a video display, and be able to send data to the supervisor computer at the same time. It also requires that the supervising computer be able to direct and accept position feedback from typically nine hundred motion commands per second and four hundred and fifty position feedback signals per second as well as deriving focus, tracking, sectioning and brightness control information from the image processor. Compromises in the speed of the image intensifier, the video camera, the video processor or the computer systems will result in lower frame rates for the final image.

The high resolution in this system is provided by the short working wavelengths of the microscope proper. This microscope system is designed to work in the UV, and in some cases the vacuum ultraviolet (VUV), spectral region while, if desired, maintaining functional capabilities in the visible and IR spectral regions. Since the resolution of a light microscope is proportion to the wavelength of light employed in image formation the use of UV and VUV light results in improvements in resolution many times the resolution possible with visible light microscopy. It is contemplated that this increase in illumination wavelength can result in the microscope being able to resolve features potentially as small as fifty nanometers.

The spectral range of the UVM, which can vary from a relatively narrow range in the UVC, to a very broad range encompassing the VUV, UV, visible and IR portions of the spectrum, which, when coupled with the dynamic selectability of spectral region, is important since it forms the contrast of the image by employing the technique of differential absorption contrast. Since different components of a sample will absorb, transmit, reflect, scatter and emit light at wavelengths that are characteristic of it's physical and chemical properties a microscope that can take full advantage of these characteristics can form images based on these differences where such differences are converted to color images where the colors of the final image correspond to the differential absorption, transmission, reflection or emission of the sample components. This type of contrast results in highly differentiated images without the requirement for the addition of any contrast media to the sample.

The real time image formation is provided by a video processor with onboard image processing and data routing capability. The video processor imports the image from the camera of the UVM. It then processes the image according to one of several algorithms chosen by the operator and finally outputs the image to a video monitor and, or stores the data on a storage media for future processing or retrieval. The real time nature of the image formation is important to allow living and dynamic processes to be followed in real time or in slow motion playback. The real time image formation requires very fast spectral source scanning capability so that sequential wavelengths of light can be employed to illuminate the sample allowing the collection of image planes corresponding to the illuminating wavelengths, which are then overlaid to produce the final image frame. In this way at least one, and as many as ten or more, image planes are processed to create each image frame. In the case of three images planes per frame, the light source and intervening optics must be able to switch illumination or mode three times in each of the thirty cycles per second in a standard video frame rate to produce a real time video output. Alternatively the microscope can be operated in monochromatic mode to maximize the number of frames available per second allowing the microscope to image the motion of fast action or rapid dynamic changes. This rapid imaging can then be replayed at slower frame rates to study the processes involved.

The living or dynamic sample commonly moves in three dimensions. These movements result in the sample moving out of the field of view and/or out of the focused plane of view. In order to follow the sample the microscope can track under computer control in both the X and Y directions of the XY plane, and the Z direction of the sample thickness. This requires either a stage system to hold the sample which can move with the same speed and repeatability as the sample in all three X,Y and Z directions or a dynamic positioning system for the optics so that they move relative to the sample. If three dimensional information on the sample is required then the computer can acquire images from a series of Z planes above and below the current plane of focus by rapidly scanning and acquiring images at intervals in the Z travel. These sections can then be reassembled into a three dimensional image by the computer image processing system. The UVM, when operated at high magnifications in the deep TV with high NA (numerical aperture, this is the numerical aperture of the objective lens) objectives, has a shallow depth of field which supports the creation of three dimensional images.

In order to make the UVM simple to operate, all of the control tasks of the various components must be under the direction of, and optimized by, the computer. Initially, the computer must establish, an initial in-focus image according to a user defined standard set of observing conditions. From this point users can depart to discover images that suite their applications. Advanced users must be able to customize the as many of the operational parameters of the UVM as possible in order to optimize the control functions and methods used to provide the images they seek.

A detailed set of descriptions of the basic and optional components employed in typical versions of the UVM follows.

Figure 2:
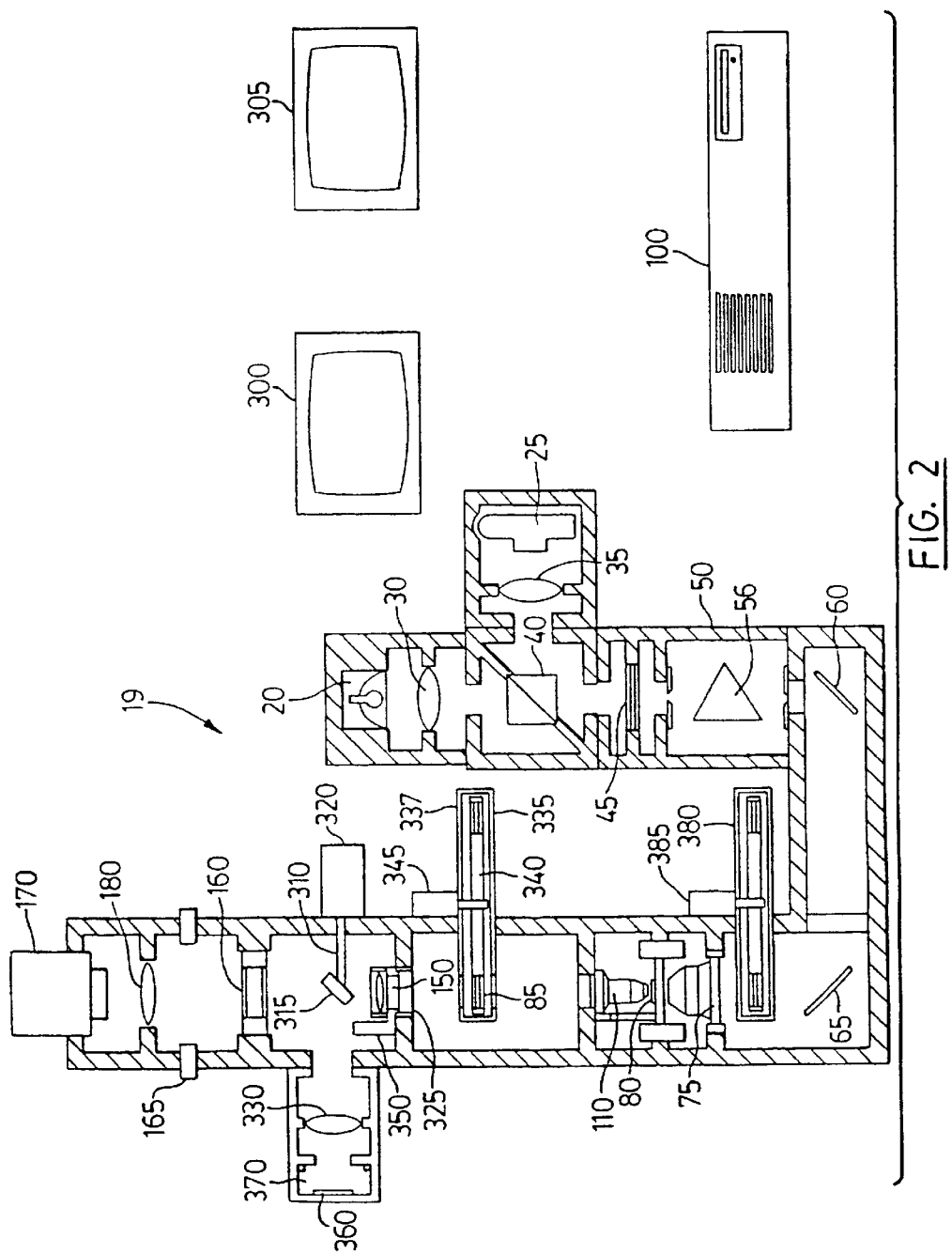
FIG. 2 shows a color translating UV microscope in accordance with another embodiment of the present invention.

The light source 20 provides the required wavelengths of UV, and in some cases, VUV, visible or infrared light, to the microscope for sample illumination. The light source 20 can be any source of photons of the required wavelengths as will be apparent to those of skill in the art. The required wavelengths are determined by the differential absorption and other optical characteristics of the sample being examined in the microscope. Light source 20 is shown in FIG. 1 as a xenon sealed beam arc source of the type made by 1LC Corporation, California, USA. In FIG. 2 and later figures the light source 20 is shown as a quartz halogen compact reflector source such as the OSRAM 64614, made by OSRAM Corporation, Montgomery, N.Y., USA.

Preferred light sources 20 for biological applications are sources which have strong UV emissions and visible emission with little or no infrared emission. Low infrared emissions result in relaxed requirements to filter the infrared from the desired light to prevent heating of the sample. The most suitable illumination choices are high power quartz halogen lamps, xenon lamps, deuterium lamps, spectral line sources such as metallic spark or capillary lamps, or low pressure arc lamps such as free argon arcs or low pressure mercury arcs with additives to produce several spectral lines.

Chemical and crystal microscopy and some biochemical applications benefit from the ability to use NIR or IR energy to obtain a wider range of spectral absorption image data. Visible and NIR illumination can be supplied by quartz halogen, or regular tungsten or other filament lamp sources. IR illumination can be supplied by black body radiators or other IR sources.

The xenon lamp provides a good low cost solution since it has a broad continuous spectrum from two hundred nanometers to twelve hundred nanometers. There are many strong emission lines in the near infrared which may need to be filtered depending on the application, by a pre-filter, from the xenon light before passing through the wavelength selection system between the lamp and the condenser.

The deuterium lamp is also a good choice since it has strong spectral emission between two hundred and three hundred nanometers and a few narrow spectral lines in the visible. The deuterium arc has very little emission in the infrared making the infrared pre-filter unnecessary in many circumstances. A deuterium lamp combined with a quartz halogen lamp makes a good source of illumination since it effectively covers the range from two hundred nanometers deep in the UVC to 2200 nanometers in the NIR. In FIG. 2 the UVM is shown with both a principle light source 20 and a secondary light source 25 which is here shown as a deuterium arc.

Several manufacturers make multispectral line spark, glow or arc lamps for calibration and scientific purposes. These lamps produce narrow spectral lines based on the filling gas mixture and on the material used in the electrodes of the lamp. Such lamps offer a simple low cost alternative to the broadband sources mentioned above, but the user is then forced to choose from the range of available spectral lines and can not choose intermediate lines for special uses.

In the UVM illumination from more than one source can be combined or selected to produce a single illuminating beam of light. The light from the first light source 20 is focused into a collimated beam by lense 30 which must be capable of transmitting the wavelengths of light that are generated by source 20 and required for image formation in the UVM. In cases such as those shown in FIG. 2 where a second light source is used the light from the second light source 25 is focussed into a collimated beam by lense 35 which must be capable of transmitting the wavelengths of light that are generated by source 20 and required for image formation in the UVM. A beam splitter operating as a beam combiner 40, here shown as a prism beam combiner, or a set of mirrors coated with spectrally selective interferences layers, or a set of automated, cycling or manually operated steering mirrors, can be used to direct the light from the sources into the final illuminating beam. Alternately a cycling mounting for the sources can be used to reposition the desired source in such a way that it produces the illuminating beam. A typical arrangement consists of a set of three sources, the first one of which is a quartz halogen source supplying the visible and UVA (ultraviolet A, light from the spectral region from three hundred and fifteen to four hundred nanometers) illumination, the second source being a deuterium arc that supplies the UVB (ultraviolet B, light from the spectral region from two hundred and ninety to three hundred and fifteen nanometers), UVC (ultraviolet C, light from the spectral region from one hundred and ninety five to two hundred and ninety nanometers) and some VUV (vacuum ultraviolet light from the spectral region of wavelengths shorter than one hundred and ninety five nanometers) illumination and a third tungsten filament lamp that provides the longer wavelength NIR illumination. The choice of source, the drive energy supplied to the source, and, where desired, the precise alignment and focussing of the source, can all be controlled by the supervising computer 100 via suitable computer controlled power supplies and positioning electronics.

In order to minimize the energy impinging on the sample all of the energy in the illuminating beam which is not required for image formation should be removed. Typically in UV and visible light microscopy applications this energy consists of NIR and IR energy which is produced by most light sources 20 or 25 and will be present in the illuminating beam. Energy can be removed from the illuminating by using hot mirrors to reflect the unwanted energy and transmit the desired energy or cold mirrors to reflect the desired energy and transmit the unwanted energy. Alternately or additionally, absorptive components such as filters or solution filled cells can be used to remove unwanted energy by absorption. The filter component to remove any unwanted energy from the illuminating beam is shown as 45.

One of the elements of the UVM is the wavelength selection system. The illuminating light can be selected by wavelength, band limit function (short pass, long pass, notch or bandpass or combinations of these functions), iris and light path to produce the desired image characteristics. For transmitted light work, the wavelengths can be chosen according to the absorption characteristics of the sample. By making suitable choices of wavelengths and bandwidths particular elements of the sample can be imaged according to their differential absorptions. For fluorescent work the wavelengths can be chosen to maximize the excitation of the sample, and thus maximize the resulting fluorescence or autofluorescence. For Raman work, the wavelengths can be selected to strongly excite Raman re-emissions. For reflected light work the illuminating beam is dynamically redirected so that it illuminates the sample through the objective lens either directly or through a special epi-illumination objective with a coaxial light path arranged around the lenses of the image forming objective lenses. The illuminating beam can also be directed into an ultramicroscopic illumination scheme where the beam is directed at the slide from an oblique angle or from a point in the plane of the slide but outside its physical extents. Several modes can be sequentially selected by the computer control system so that the final image is an overlay of images produced using fluorescent, Raman, transmitted, reflected or other images in various wavelengths.

There are several ways to implement the wavelength selection system 50. The wavelength selection can be made by a monochromator with a computer controlled wavelength drive system in the form of a stepping or servo motor. Another form of single monochromator can employ a computer controlled scanning or vibrating mirror to select the desired wavelength. A third variation uses a linear array of optoelectric shutters such as a series of Kerr cells or liquid crystal light shutters to select the desired wavelength. The actual dispersing component in the monochromator can be a prism 56 in FIG. 2, a grating 55 in FIG. 1, or a combination of more than one grating or grating and prism, or an acousto-optical grating. The bandwidth of the monochromator can be controlled by a variable slit, a variable iris or a tilting mirror. The monochromator can be replaced or augmented by a cycling set of illumination filters where the filters can be bandpass, shortpass or longpass filters constructed as interference transmission or reflection filters, interferometers, wedge interference filters, or ionically colored glass filters. The illumination filters can rotate in a filter wheel as shown in FIG. 2 where the illuminating filter wheel 380 is similar in construction to the intermediate filter wheel 335 described in detail later. Alternately the filters can vibrate in a cycling mechanism. These filters can serve as order sorting filters for the monochromator or can perform the entire task of light filtration removing the need for the monochromator.

FIG. 2 shows another embodiment of the present invention wherein a rotating filter wheel 380 is added between the source of the illuminating beam and the condenser to rapidly filter, to compensate the intensity of, or to selectively reflect wavelengths of light prior to reaching the condenser. In some cases the use of the filter wheel 380 can allow the removal of the monochromator 50 and filter 45. The filter wheel is driven by drive motor 385 which can be an alternating current synchronous motor or a direct current motor or a servo motor or a stepper motor, any of which would be under control of the computer 100.

Light from the wavelength selection system 50 is reflected by mirrors 60 and 65 to direct it towards the condenser 75 and sample 80. Alternately in reflected light applications the light may be redirected by movable mirror 90 mounted on positioning shaft 115 and reflected by mirror 95 into beam combining prism assembly 105 which directs the illuminating beam into objective 110 and then onto the sample 80. Mirrors 60 and 65 may be coated with interference filter coatings which perform some or all of the light filtering operations especially in specialty purpose built UVMs for clinical applications where a standard set number of wavelengths of light are desired for imaging. Using mirrors 60 and 65 as the illuminating filters may remove some or all of the need for filter 45 or monochromator 50.

Polarizing means in the form of polarizing sheet film or of any of the commonly available polarizers which can transmit and effectively polarize the light in the illuminating beam can be used in either or both of the illuminating path between the source and the sample, or in the path between the objective and the image intensifier to give polarization and rotary information on the optical rotary power of the sample. A polarizer in the illuminating beam is shown as 70 or can be incorporated as part of rotating filter assembly 380, and a polarizer in the image beam can be incorporated as part of filter assemblies 85 or as part of rotating filter assembly 335. These polarizing means can be fixed or can be rotating or vibrating in one of the sample or intermediate filter sets or they can be rotating in their own filter sets synchronized with the other filter sets. It may be desirable to use an analyzing polarizing component between the objective and the image intensifier to resolve the optical rotation or state of polarization of a sample. This analyzer can be manually or computer controlled. For UV operation crystal polarizers with air spaced (as opposed to cemented) components consisting of calcite or crystal quartz can be effective.

A mirror system under computer control can be implemented to couple a laser beam into the illumination path between the monochromator and the filter wheel. The mirror must be mounted on a fast operating mechanism so that it can be coupled into the path in synchrony with the frame rate of the imaging system. Alternately a notch rejection filter in the illumination filter set can be used to eliminate the laser beam from the illuminating beam when it is not being used to form an image. The laser beam is particularly useful to add Raman or confocal information to the image and for tracking moving samples in darkfield illumination where only a small portion of the image is required to be illuminated.

Figure 15:
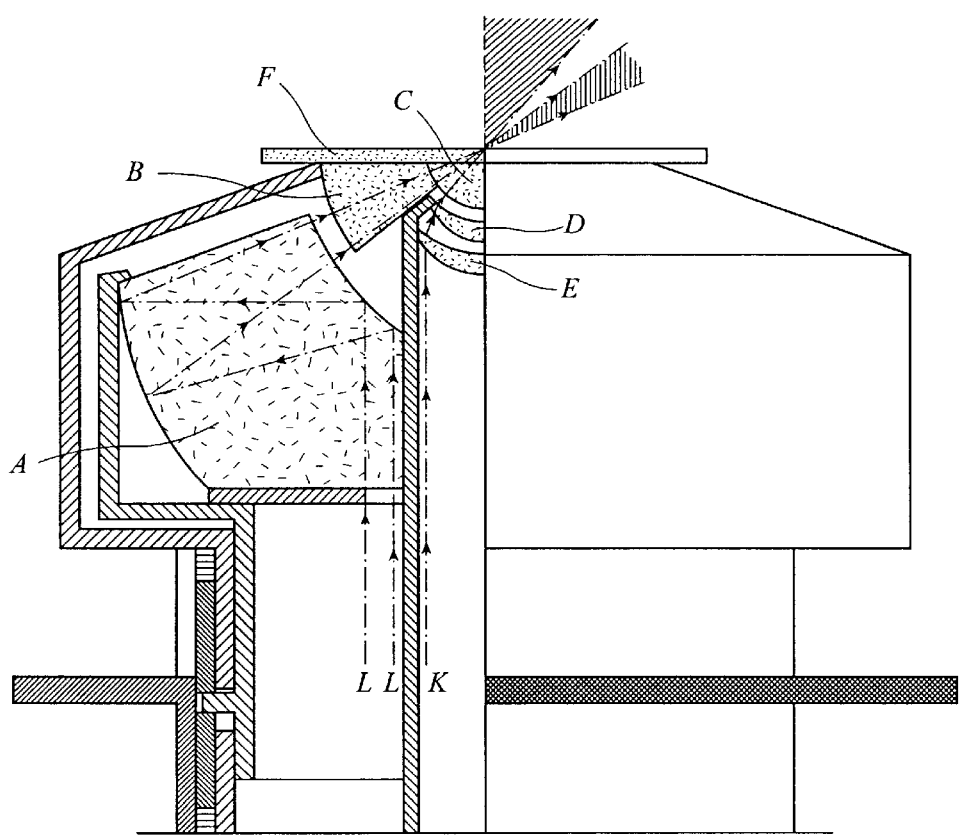
FIG. 15 is a reproduction of FIG. 113 of J. E. Barnard's book "Practical Photomicrography", Edward Arnold & Co., London, Third Edition, 1936, which shows a preferred implementation of a brightfield and darkfield condenser for use with various embodiments of the invention.

Once the illuminating beam passes out of the illumination filters or monochromator, a beam steering mirror can be used to send the beam on a transmitted or reflected light illumination path. The 'transmitted light path sends the light through the condenser and through the sample to the objective, or in the case of darkfield the light is directed through a coaxial darkfield condenser or a standard darkfield condenser, while the reflected path sends the light through the objective, or through a coaxial illumination system arranged around the objective in the case of reflected darkfield. A presently preferred UV and visible light capable coaxial brightfield and darkfield condenser is described in J. E. Barnard's book "Practical Photomicrography", Edward Arnold & Co., London, Third Edition, 1936, page 302, FIG. 113 and related text and the contents of this publication are incorporated in this patent. Referring to FIG. 15, which is a reproduction of FIG. 113 in Barnard's "Practical Photomicrography", the preferred brightfield and darkfield condenser is described by Barnard on pages 301 and 302 as follows:

"The [condenser] [provide]s a means of focussing the object in visible monochromatic light by dark-ground illumination and then changing over to transmitted ultra-violet light illumination. This condenser is a composite one and consists of a high aperture dark-ground illuminator mounted concentrically with and encircling a quartz condenser. The former secures visibility in ordinary light and is used for purposes of search, location and primary focussing. The latter is available for use with any suitable ultra-violet radiation and enables a transmitted light image to be secured. FIG. [15] shows the appliance in section. Visible light enters as shown at LL, the centre of the beam being stopped out by a removable plug which allows only an annular beam to enter. This beam is twice reflected in the glass reflector A and reaches the object after passing through the front lens C of the central quartz condenser. Thus the object is seen illuminated on a dark-ground and can be focussed. When it is desired to photograph the object in ultra-violet light the central stop is removed and replaced by a tube carrying an annular stop which allows the ultra-violet light K to enter the central quartz condenser only, E D C. The quartz object slide is shown at F. Thus the condenser is focussed on the object primarily in visible monochromatic light, and by simply changing the stops ultra-violet light is focused on the object ready for photography. The foci of the two systems are similar, but exact par-focality is secured by actuating the knurled ring which adjusts the dark-ground illuminator only."

Figure 16:
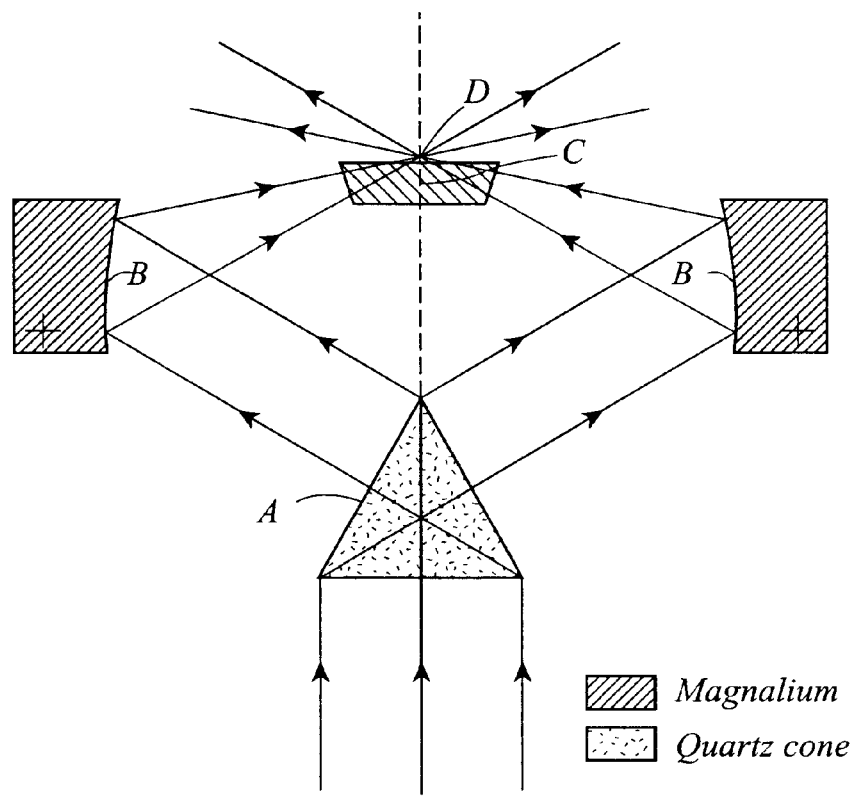
FIG. 16 is a reproduction of FIG. 114 of J. E. Barnard's above-mentioned book, which shows a preferred implementation of a darkfield only condenser for use with various embodiments of the invention.

A presently preferred UV darkfield only condenser is described on page 303, FIG. 114 of the same publication and which is also incorporated herein. Referring to FIG. 16, which is a reproduction of FIG. 114 in Barnard's "Practical Photomicrography", the preferred darkfield condenser is described by Barnard on pages 302 and 303 as follows:

"FIG. [16] shows in section the principle, the method of construction, and path of rays [for the darkfield condenser]. A beam of ultra-violet light is thrown on to the base of a quartz cone A, and is internally reflected on to an annular magnalium reflector B. The reflecting surface B, is of such curvature that the light is concentrated at D after passing through the quartz lens C. D is the position occupied by the object, and at that point practically the whole of the light passing through the quartz cone is focused on the object. Thus there is no loss of light, such as occurs with any form of annular illuminator. This appliance [enables one] to obtain photo-micrographs of small living organisms in ultra-violet light by dark-ground illumination with exposures as short as 5 seconds. It also works well with visible light and is used for preliminary searching and focussing."

The condenser 75 can be positioned for centration in the X-Y plane and for focus in the Z direction manually or by a system of three single axis drives or by a combination drive system, shown as 72 in FIG. 1, under computer control. This drive (or drives) can be an electric, hydraulic, pneumatic, piezoelectric or any combination of these positioning systems. The hydraulic and pneumatic drives have the advantage of removing external electric and magnetic fields from the area of the sample and so removing any external influences that these fields may create. Alternately the condenser 75 can be preadjusted for centration and alignment with the objective 110 and stage 130.

An aperture and a scanning system can be used to implement a flying spot microscope by placing these components between the wavelength selection system and the condenser (in transmitted light applications), or the beamsplitter or mirror (in reflected light applications). The flying spot method of illumination can be used to reduce the illumination of the total sample by scanning the illuminating beam. Another application is for selective microbeam irradiation studies where it can be used to study selectively the effects of a small beam of light of a given wavelength and bandpass on the sample. In this method the beam is scanned over the entire sample to produce a pre-irradiation image then the beam is scanned or parked on the part of the sample to be irradiated. After the desired period of irradiation has passed the scanner area is increased or shifted so that the irradiated area can be compared to the non-irradiated surroundings.

Figure 7:
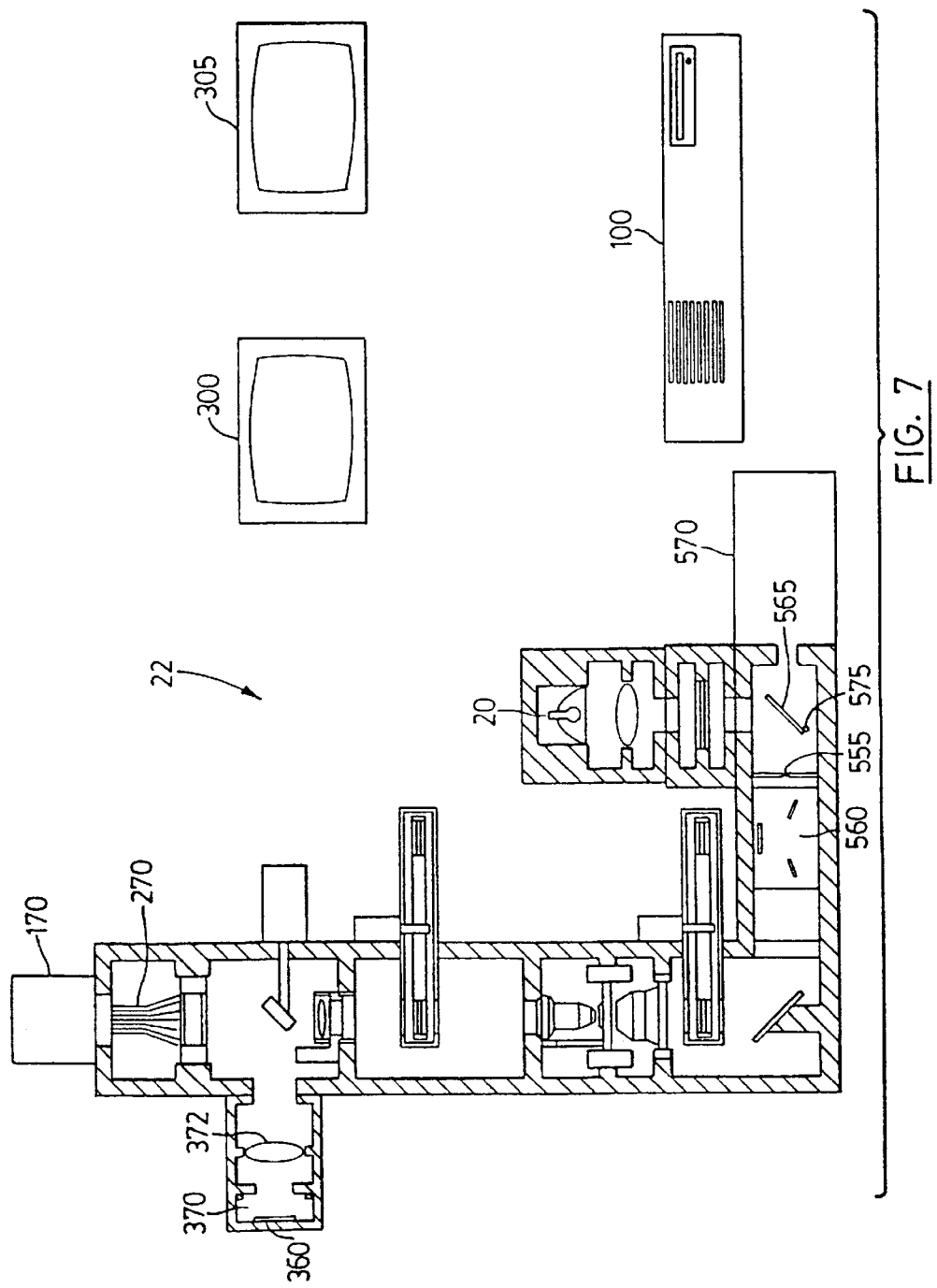
FIG. 7 shows a color translating UV microscope in accordance with another embodiment of the present invention.

FIG. 7 shows another embodiment of the present invention which is similar to that shown in FIG. 2 except wherein an aperture 555 and a scanning system 560 have been added in the illuminating beam path to scan the illuminating beam over the sample area under control of the computer 100. The scanning system can use a UV or multispectral laser source 570 instead of the monochromator 50 and related filters 45 and light sources 20. The multispectral laser source 570 would contain at least one wavelength in the UV for differential absorption imaging. The scanner can be any of the commonly available rotary mirror, galvanometer based mirror, solid state micromirror or vibrating mirror types, under the control of the supervising computer.

The sample 80 is commonly mounted on a slide 120 and covered with a cover glass 125 and, as such, it is readily adaptable to oil immersion techniques. Alternatively, and depending on the particular application, the sample may be mounted directly on the stage of the UVM as in metallography or may be used in an uncovered form such as direct immersion microscopy or may be living samples on a slide, well slide, or petri dish. The slide 120 or other support for the sample is in turn supported by the stage 130 of the microscope.

The stage 130 employed with this microscope can be a conventional stage however, for the very high resolution which this system is capable of, the stage should be of a computer controlled nanopositioning type. The stage can be moved in the X-Y directions under the control of the computer 100 to accomplish positioning of the sample and to facilitate tracking of moving samples in the sample. In the tracking mode the computer 100 analyses the image and, based on the analysis, locks on to the target component of the sample which it is desired to track and issues positioning commands to the X-Y stage drives 135 to keep the target area of the sample 80 within the field of view and preferably centered in the field.

The stage 130, or alternately the objective 110, is also controlled by the computer 100 with regard to its Z position. The Z position controls the focus of the system. The Z position can also be used for optical sectioning of the sample to provide information to the computer 100 that it can then use to reconstruct a three dimensional image. When high NA objectives 110 are used in the UVM, very thin optical planes can be imaged. Past experiments indicate that sections as thin as 0.1 micron or thinner are achievable. If, for instance five optical sections are collected above and five sections below the perceived center height of a spherical sample then the computer 100 can recreate the contours of the sphere in three dimensions for display on the computer monitor by processing and reassembling these sections into a final image. Components within the sample can move in the Z direction as well as the X and Y direction during tracking so the Z stage positioning system can also be interfaced to the X and Y tracking drives from the computer so that it follows the sample movement in all three directions. While long term tracking of the sample is taking place the computer can switch the illumination to a wavelength, bandwidth, intensity and duty cycle which minimizes the effect of the illumination on the sample by controlling the illuminating filter wheel 380 or the monochromator 50 or the source 20, and 25 if employed, intensity. The computer can also take images at intervals under full illumination conditions to give a time lapse indication of what has occurred in the sample.

Figure 3:
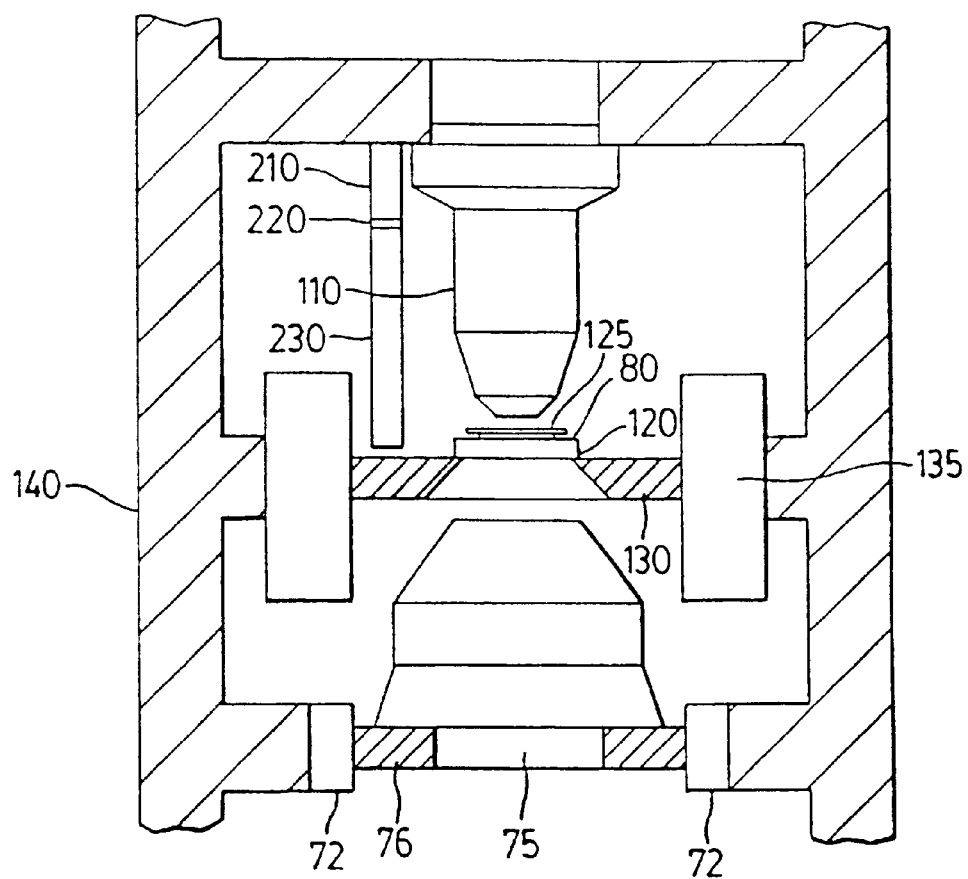
FIG. 3 shows an embodiment of a microscope stage for use with a color translating UV microscope in accordance with the present invention.

A stage position feedback system is also shown in FIG. 2 and in more detail in FIG. 3 where a capacitive probe 230 is coupled capacitively to the stage 130. The probe 230 is isolated from the microscope frame by insulating section 220 mounted on support 210. FIG. 3 shows an enlarged view of an embodiment of the sample part of a UVM in accordance with an embodiment of the present invention. The sample 80 is mounted on a slide 120 and covered with a cover glass 125. The slide is supported by the stage 130 which can be moved in three dimensions by the positioning drive 135 under computer 100 control. Spatial scanning is accomplished by X and Y movements of the stage. Focussing and optical sectioning for three dimensional reconstructions are provided by Z direction movements of the stage. The condenser 75 is mounted on a supporting ring 76 which is positioned in three dimensions by drive system 72 under manual or computer 100 control. The distance between the objective 110 and the stage [and hence the top surface of the cover glass in slides or samples where the distance from the stage to the top surface of the cover glass is accurately controlled or known] is monitored by the capacitive probe system where the capacitive prove 230 is capacitively coupled to the stage 130 to provide distance information based on the capacitance of the gap between the flat surface of the probe and the stage. When this system is used with slides systems of known and accurately controlled thicknesses then the capacitive probe 230 provides a feedback signal to computer 100 to allow automatic focusing.

It is presently believed to be advantageous for the design to take into account sources of external magnetic and electrical fields passing through the sample and eliminate or minimize them. This can be accomplished by electrostatic shielding of the sample area. A magnetic path can be introduced around the sample area to minimize any magnetic field in the sample area. The magnetic shielding can be accomplished with specialty magnetic alloys, such as mu metals, or alloys containing iron, alternately ferrite layers can be employed in the inner tubular housing design. The minimization of these fields helps to ensure that the sample is not being influenced by external factors which might give a misleading impression of the sample's normal function in its usual environment. Electric fields, magnetic fields, light levels and wavelength, acoustic fields, temperature and pressure at the sample must all be taken into account when considering whether or not the sample is experiencing conditions similar to those it would normally find in vivo. The stage in an automated microscope can produce intense magnetic fields from drive motor components, intense electric fields from piezoelectric drives and acoustic fields from the same source since any alternating current component in the piezoelectric drive voltage will be converted into a displacement with a resulting acoustic component. For the very high magnifications and resolving power that the UVM makes possible it becomes more important to eliminate the sources of external fields since they can act to displace or vibrate components of the imaging optics or of a living sample thereby affecting image quality.

To take full advantage of the increases in resolution offered by the short wavelengths of the UV light employed it is desired to provide a very stable supporting system so that there are no vibrations or other motions of the sample relative to the image forming optics, image intensifier and video camera. The resolution of a UV microscope with a 1.3 NA objective operating at two hundred and fifty nanometers will be in the order of one hundred and twenty nanometers. The UVM can employ standard C shaped microscope frames and can be retrofitted to existing microscopes by changing the required optical components. While the UVM can be constructed on a standard microscope C shaped frame, it is generally not preferred, as the UVM will suffer from degradation of the image due to vibration, which is also true if the UVM is retrofitted into an existing C frame microscope. For the best image performance it is desired to provide a support with as little vibration as possible. For this reason past attempts at UV microscopes designed for the best possible resolution have taken great pains to isolate the image forming components from vibration and have typically been constructed using a massive three point mounted optical bench with or with out passive or active vibration isolation. This style of construction typically resulted in a large and costly form of design. The presently preferred design for the present invention is to use a very rigid and vibration damped tubular housing 140 which transmits vibration equally to all the image forming components and the sample. In this way the whole unit can be subject to vibration but the vibration will be substantially identical in amplitude, and phase for all of the critical image forming components.

Since some versions of the UVM design require the use of a rotary or oscillating filter drive or drives, it is preferred to mount the drive outside and not in direct contact with the tubular frame of the imaging components of the microscope. In such a design the drive components are mounted in a second outer tube which also supports the inner tube on vibration damping mounts. The rotating filters project into the inner imaging tubes through slots in the tube wall and do not come into direct contact with the inner tube at any point. The outer tube also serves as a light and dust tight housing to keep stray light and dust from contaminating the image or the components in the imaging tube.

The UVM can use a single fixed objective lens 110 or it can use a rotary nosepiece containing more than one lens. The nosepiece can be under manual or computer 100 control. Alternately it can use a slider on a circular path to switch between two or more lenses. The objective lens 110 or lenses used in the UVM must be capable of transmitting the wavelengths of light employed in the system. Reflective, refractive or combination objectives can be used. Lens materials include quartz, calcium fluoride, lithium fluoride, sapphire, or spinel or any other suitable glass or crystalline materials. In order to take full advantage of the higher resolving power of the UV light the most applicable objectives will generally be the high power immersion lenses. Keeping the NA of the objective lens high is also important due to the effect of NA on the resolving power and the depth of field of the system. Optical sectioning for three dimensional image formation requires the shallowest depth of field possible. For applications which do not require anything but visible and UVA operation this system can use conventional glass lenses which have been tested and selected for UVA use.

Figure 8:
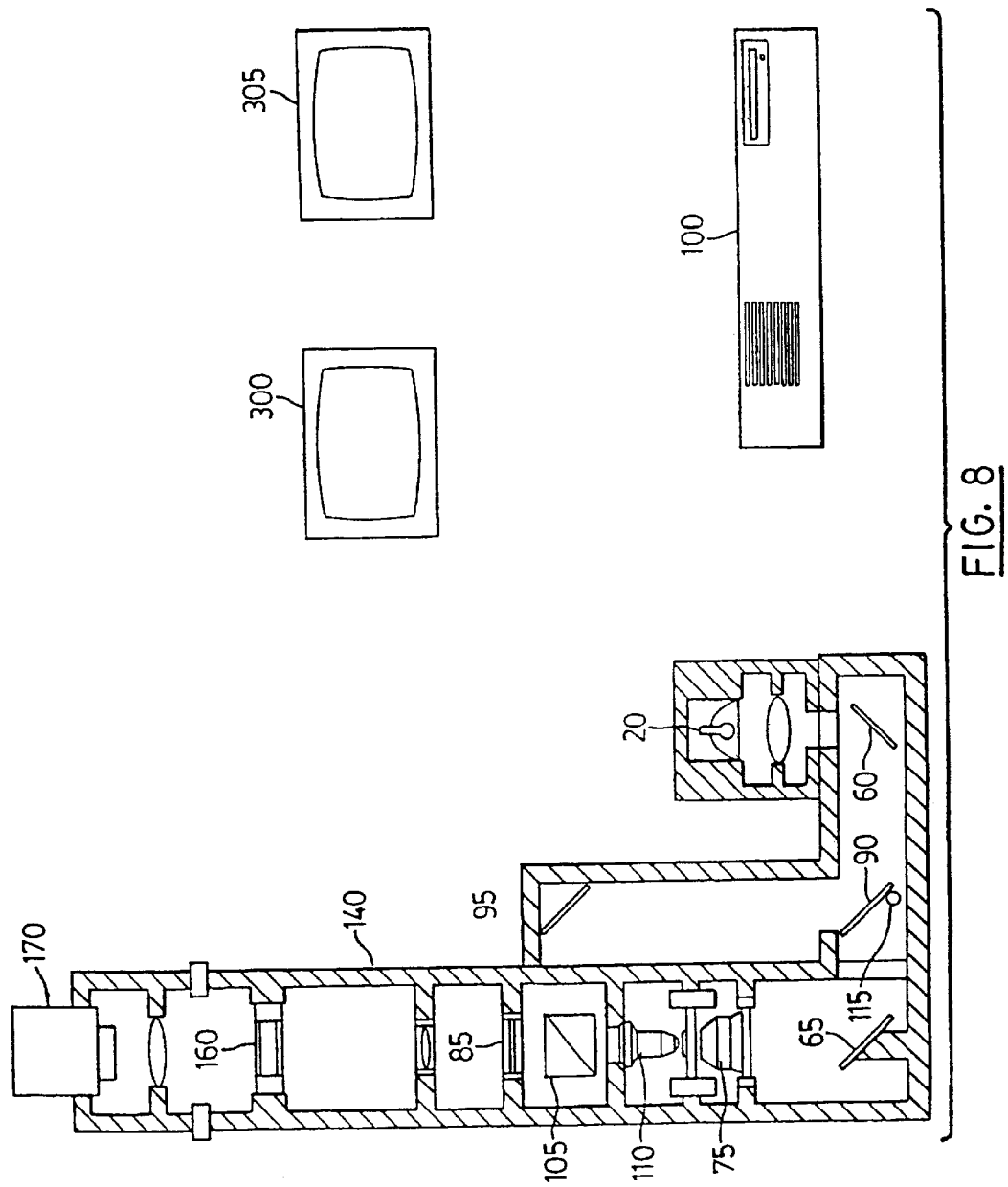
FIG. 8 shows a color translating UV microscope in accordance with another embodiment of the present invention.

FIG. 8 shows an embodiment of the present invention which is similar to that shown in FIG. 1 except that a system of mirrors and a beamsplitter have been added to allow the illumination path to be switched from transmitted to reflected light under computer control. The mirror 90 can be moved into position to intercept the illuminating beam by actuating shaft 115 which can be controlled by a cam, motor, solenoid, hydraulic or air actuator controlled by the computer 100. When the mirror 90 is in the reflecting position, the illuminating beam is directed via mirror 95 to the beamsplitter 105 acting as a beam combiner which directs the illuminating light down through the objective 110 to accomplish reflected light microscopy. The mirror 90 is arranged to be driven so that it can be cycled into the beam path many times per second, or alternately the mirror 90 can be arranged on a rotating wheel arranged as a light directing chopper wheel.

Vacuum UV capability can be added to the UVM by adding suitable light sources 20 or secondary light sources 25 such as metallic spark sources, along with suitable optics. The microscope must be able to convey the VUV illumination and image information to the image intensifier which can be accomplished by purging all the light paths between the source and the sample, and between the sample and the image intensifier, with dry nitrogen or other gases which do not absorb in the VUV region of interest. This is necessary since the oxygen in the air strongly absorbs UV light below about one hundred and ninety seven nanometers. The lenses in a VUV version of the UVM must be constructed using reflective objectives and optics or they must use refractive materials that transmit at the wavelengths desired. Reflective optics have been the optics of choice for VUV use since they exhibit no chromatic aberration and can perform equally well over a very wide spectral range. Typical choices for VUV refractive system optical components are lithium fluoride, calcium fluoride and sapphire. A VUV version of the UVM operating with an objective of an NA of 1.4 at one hundred and twenty five nanometers will be able to resolve samples fifty five nanometers in diameter or less.

The use of this system in scanning mode in much the same way as a confocal microscope with a small point of light will increase this resolution further. The computer can electronically remove all the image information except the single pixel corresponding to the scanning position of the point of light to achieve performance exceeding that of a traditional confocal microscope. This version of the UVM which uses very short wavelengths with their attendant reflective optics and special transmissive components can, when coupled to the differential absorption capabilities of the microscope in this wavelength range, produce the highest possible resolution and image quality achievable with a "light" microscope. Further gains in resolution and consequently magnification are possible by using soft X-ray sources and optics. In the VUV version of the UVM the slide must be coupled to the condenser with a suitable VUV transmitting fluid and the coverglass must be coupled to the objective with the same fluid. The sample must also be mounted in a fluid or mountant which is transparent to VUV of the desired wavelengths. A discussion of vacuum UV optics for microscopy and a review of the subject is found in "Microscopy in the region of wavelength 2,000 to 1,000 angstroms", B. K. Johnson, (1953), 73:24–29, Journal of the Royal Microscopical Society, London and the contents of this publication are incorporated herein by reference.

After the light from the sample is collected by the objective lens 110 an intermediate filter set 85 can be used to isolate components of the light transmitted by, or originating from, the sample. It is common for biological materials to exhibit broadband blue autofluorescence when illuminated by a short wave UV light source 20. This autofluorescence can be strong enough to fog the desired UV image. It is therefore important to remove the blue autofluorescence from the image prior to it encountering the image intensifier 160. The UV image can be isolated from the autofluorescent image by employing a UV transmitting and visible absorbing or reflecting filter between the objective and the image intensifier. As mentioned above this filter set 85 can incorporate polarizing components or it can be desired to mount an analyzing polarizer under computer 100 control and separate from the filter set. Alternately any of the intermediate filters or polarizing components can be mounted in a rotating filter set. Such a rotating filter set is shown as 335 in FIG. 2 where the outer light tight housing contains an inner rotating filter holding wheel 340 with several filters 85 mounted in it. The light from the objective 110 passes through a second rotating filter wheel which is substantially the same as the filter wheel described earlier in this paragraph. The filter wheel is driven by motor 345 which can be any of the motor types described above which can be controlled by computer 100 or can be manually selected.

Alternatively, it may be desirable to study the fluorescent or autofluorescent components of the light emitted by the sample due to internal chemical components of the sample or due to fluorochromes added to the sample. This is done with filters which transmit the wavelengths of the fluorescence or autofluorescence and block the exciting UV wavelengths. It is also possible to employ narrow band notch rejection filters to observe the Raman re-emission wavelengths from the sample. In Raman microscopy a high power monochromatic, polychromatic or narrow band source, such as a laser or filtered lamp, is used to excite the sample which then re-emits lights at other wavelengths determined by the chemical and physical characteristics of the sample. Then a Raman notch filter 85 situated in the image path between the objective and the image intensifier attenuates the narrow band exciting wavelength in order to allow the Raman emissions to be viewed at wavelengths other than the exciting wavelength.

In an infinity corrected version of the UVM the next component in the optical system is a tube lens 150 to convert the infinity focused image to a fixed focal point image on the input screen of the image intensifier 160 or video camera 180 in cases where an image intensifier is not used and the image is focused directly onto the sensitive surface of the video camera 160 by the tube lens 150. It may be desirable to control the exact position of the tube lens 150 and consequently the focus of the image on the input screen of the image intensifier 160. In order to accomplish this a Z positioning drive 350 can be used to move a mount 325 holding the tube lens 150. The tube lens 150 is moved to control the focus of the image on the input screen of the image intensifier by Z positioning drive 350. The process of focussing the video camera on the output screen of the image intensifier is assisted by projecting an alignment pattern from target 360 illuminated by light emitting diodes located at 370 and shining on target 360 onto the input screen of the image intensifier. The pattern is imaged with lens 330 via mirror 315 which is moved into position on the optical axis by positioning drive 310 and 320 under computer 100 control. The image is reflected on to the image intensifier by movable mirror 315 which is located on the end of the movable shaft 310 which is positioned by drive 320.

If an image intensifier 160 is used, it fulfills two functions in this invention. Firstly, it converts any light within the spectral sensitivity range of the photocathode to light of spectra determined by the phosphor used on the output screen, this conversion is typically used to convert UV, VUV or IR light into visible light. Secondly, it provides photon gain between its input and output allowing much less light to be used to form the image of the sample, this means that the sample is exposed to much less light than in a normal light or UV microscope. This is particularly important in UV microscopy since UV light in the regions below three hundred and eighty nanometers can have strongly detrimental effects on living samples. The use of the image intensifier tube reduces this exposure to values typically 1/10,000 of the intensity normally required to form an image. The image intensifier can be a proximity focused diode design or a single or double microchannel plate design or any other type of image intensifier. The double microchannel plate image intensifier offers the highest photon gain but at the expense of resolution and signal to noise ratio. The double microchannel plate type, operating at the highest possible voltage, is chosen when greatest light gain and consequently the least possible interference with the normal activities of a biological sample is desired.

The choice of an appropriate input photocathode for the image intensifier 160 is important to the efficient operation of the UVM since different photocathode materials exhibit widely varying spectral sensitivities. Phosphors are available in a wide variety of emission wavelengths and emission efficiencies. In order to accomplish the highest efficiency in the transfer from input light to output light a high efficiency phosphor such as P20 must be used, in combination with a photocathode optimized for operation in the spectral region of primary interest. For instance, short wave UV conversion requires a photocathode that is sensitive in the deep UV such as the S20 photocathode. Visible or extended red operation, for fluorescent, autofluorescent or Raman imaging, requires the addition of other sensitive materials to the photocathode such as those used in the current multi-alkali systems. Visible insensitive image intensifiers, commonly described as solar blind, provide UV images without the interference from visible autofluorescence from the sample. In general a good choice of photocathode is one which exhibits wide spectral bandwidth and high sensitivity.

Figure 4:
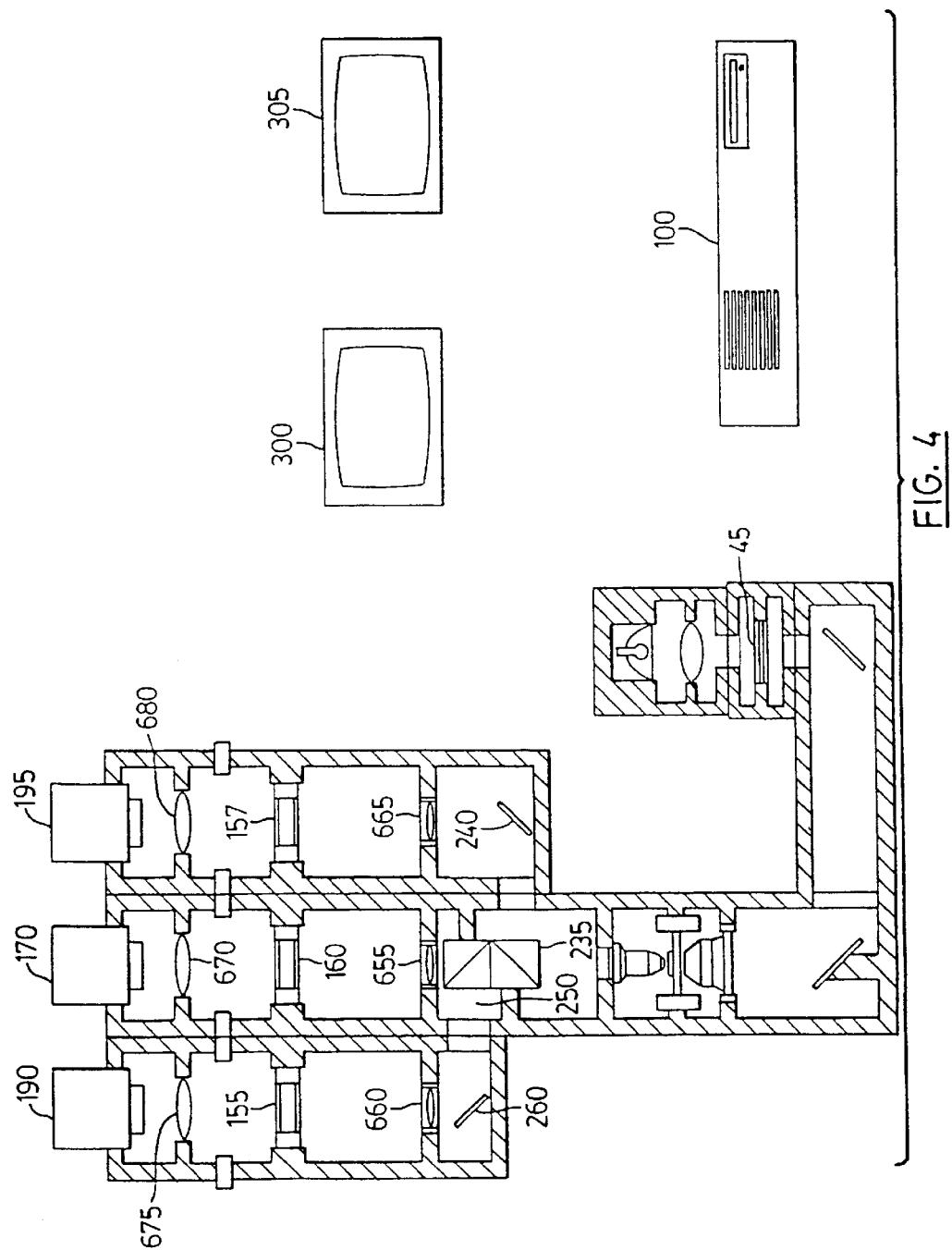
FIG. 4 shows a color translating UV microscope in accordance with another embodiment of the present invention.
Figure 6:
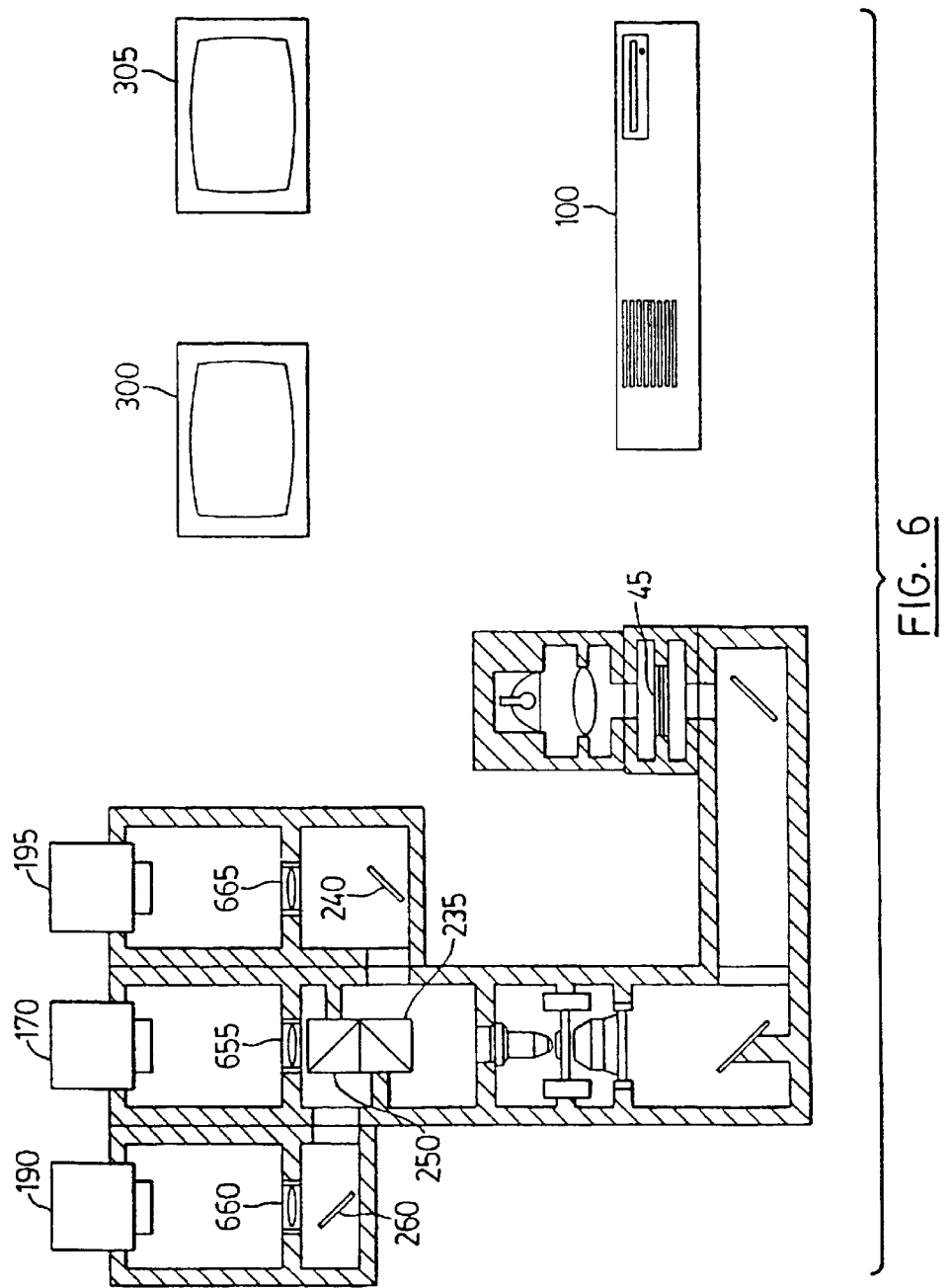
FIG. 6 shows a color translating UV microscope in accordance with another embodiment of the present invention.

In some cases such as are illustrated in FIGS. 4 and 6, it may be necessary to arrange for more than one image intensifier to be positioned in the optical path to allow for operation over a wide spectral range. In FIG. 4 three image intensifiers 155, 160, and 157 are provided with three wavelength ranges of signal by dichroic beamsplitters 235 and 250 and mirrors 260 and 240. The resulting intensified image is directed to cameras 190, 170 and 195.

FIG. 4 shows a triple imaging system embodiment of the present invention. In this case, three image intensifiers 155, 160 and 157 and three video cameras 190, 170 and 195 with their related filtering beamsplitters 235 and 250, tube lenses 655, 660 and 665 and relay lenses 670, 675 and 680 receive parts of the video spectral information. The benefit of this system is high imaging speed. For example where the video camera is capable of eighty frames per second this configuration allows the computer to assemble three image planes into a final color image eighty times per second for a final frame rate of eighty frames per second instead of the [eighty divided by three]0 frame rate for a single camera using a series of sequential image planes as in the previous figures. The multi spectral light in the image from the objective 110 is divided into its spectral components by beamsplitters 235 and 250 which may or may not contain dichroic coatings on the hypotenuse of the beam splitter or interference filters on the external surfaces. The light which goes straight through the beam splitter reaches the center system while the light reflected at the beam splitter is then reflected through ninety degrees by the mirrors 240 and 260 into the two outer systems. The mirrors 240 and 260 can be coated with interference filters so that they are selectively reflecting for certain wavelengths in which case they can perform part of the filtering function. In this type of system it may be necessary for the monochromator to provide several wavelength regions simultaneously so that the required three spectral ranges are available to be separated.

As the output of the image intensifier is a phosphor screen, it represents a lambertian source and light from this screen must be transferred or relayed to the observer or video camera. This relay can be done with a relay lens 180 which has the disadvantage of low collection efficiency, or it can be done with a fiber optic relay bundle or taper shown in figure two as 270, commonly known as a minifer, which is able to collect a substantially increased amount of the light emitted by the output phosphor screen of the image intensifier 160 and directly convey it to the video camera 170.

Figure 5:
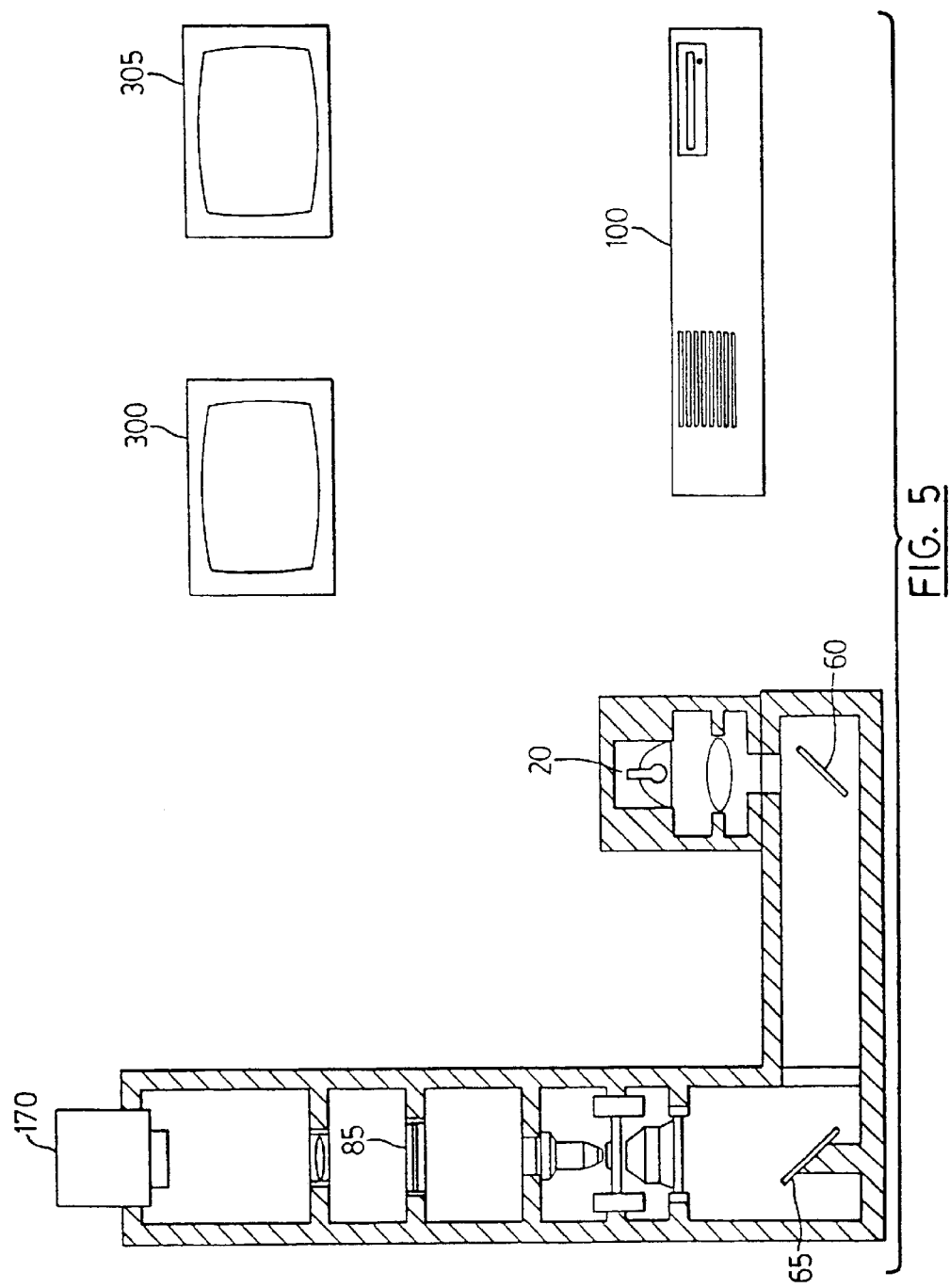
FIG. 5 shows a color translating UV microscope in accordance with another embodiment of the present invention.

Normally the UVM would use a single CCD monochrome analog camera or a single CCD monochrome digital camera such as a DALSA CA-D4 which is a 1024×1024 pixel design. FIG. 5 shows another embodiment of the present invention. In this example, a UV sensitive video camera such as a lumigen or Unichrome coated CCD or a photodiode array camera or a photodiode/CCD hybrid camera or a tube camera 170 is used alone to form the image plane information. In this case there is no image intensifier required to carry out the spectral color translation from UV, visible or NIR, to visible. The disadvantage of this system is that the sample will receive an amount of light that is greater than the system which utilizes an image intensifier such that the increase in light will be equal to the gain of the image intensifier. Due to the increase in light, it is contemplated that this type of UVM system is more suitable for non-living applications such as metallography, semiconductor imaging, crystallography, microspectrophotometric imaging of fixed biological systems, light stable and/or resistant samples.

FIG. 6 shows a similar arrangement except the system does not employ image intensifiers but instead uses video cameras which are directly sensitive to the wavelength ranges used for image creation. Alignment and vibration can present real problems to the successful accomplishment of this type of arrangement and consequently the arrangement of figure two is preferred. Alternately a sliding circular track can be used to position one or more image intensifiers in the optical path. In the case where a sliding track positions the image intensifier it may be desirable to put a relay lens in one position of the sliding track to transfer visible and NIR image information directly to the video camera bypassing the image intensifier. FIG. 6 shows another three camera embodiment of the present invention which is similar to that of FIG. 4, but without image intensifiers as in FIG. 5. Here three UV sensitive cameras 170, 190 and 195 are used to generate the image planes. In the same way as figure five above this system has reduced sensitivity but high frame rates as in figure four.

For direct viewing of the image intensifier output, it is possible to utilize a standard microscope binocular or trinocular after the image intensifier. If this direct viewing system is implemented, a slider can be used to hold the image intensifier or image intensifiers and exchange the position of these items with a compensating lens to directly send the image information to the video camera or to the trinocular or binocular. In such a system the microscope functions as a normal microscope in the visible and fluorescent modes of operation and can then switch to UVM operation for non-visible and image intensified work.

Depending on the type of final optical system employed it may be necessary to effectively block UV light from reaching the operators eyes through the binocular or trinocular system. This can be done with UV blocking filters such as Schott glass WG-370 or similar products. UV light can also lead to fluorescence in the optical components of some objectives, condensers or eyepieces. This is another reason why optics for the UV microscope must be specially designed for the best possible image formation.

A second area of UV exposure concern is the sample and stage area, illuminating light path and source housings. All of these areas need effective blocking components to ensure that UV light does not leak into the working area outside the UVM. A UV interlock and guard can be used to reduce or eliminate the possibility of user exposure to the UV light at the sample area of the microscope. The guard consists of a UV opaque shield which prevents UV glare from reaching any point where the eyes of the microscopist or an observer could potentially be located. Alternatively, or additionally, an automatic shutter consisting of a UV opaque material in the illuminating path can be used to remove UV from the illuminating beam when the sample area guard or, in some versions of the UVM the sample holding chamber area, is open.

If a trinocular is provided for direct visual observation of the output of the image intensifier, where the image intensifier intercepts the image from the sample, any UV light from the source can not normally pass through to the observer from the sample so the eyepiece may not have to filter all the UV from the image. Careful analysis of all the spectral emission from the image intensifier phosphor and then to effective filtering of any unwanted wavelengths will greatly enhance the contrast ratio and the apparent focus of the final image. The eyepiece can be a monocular, binocular or trinocular system commonly used in light microscopes or any other viewing arrangement such as would be obvious to one skilled in the art of microscopy.

High speed and gated image intensifiers can be used for tracking or freezing the motion of fast moving samples. In this case it is important to choose the output phosphor of the image intensifier with due consideration to the required response speed of the phosphor. The decay time of the phosphor must be sufficiently short that the image from a previous image plane does not persist into the time interval for the following image plane. In order to provide stop motion effects for freezing the motion of a rapidly moving or oscillating sample either the image intensifier can be gated at precise intervals by external electronics, or the illuminating light path can be shuttered by a controllable shutter. The shuttering can also be used for dose reduction or selective wavelength elimination or can be used for dose reduction on the basis of the relative destructive effects of various doses at various wavelengths. For example, the illuminating shutter can be opened only twice per second during the least harmful wavelength of a set of wavelengths making up a frame interval while the microscope was being used for searching and, once the desired sample is located, then the full range of wavelengths is allowed to pass.

Alternatively, neutral density filters can be introduced into the illuminating beam path during searching or long term tracking of components to reduce the exposure of the sample. The neutral density filter is chosen to provide an image only slightly above the perception limit of the observer's eye or above the noise floor of the CCD. Once a sample of interest is located the filter is removed allowing the image intensity to take more complete advantage of the available dynamic range of the observer's eye or the CCD. Neutral density filters which absorb the energy not transmitted can become very hot so they may need to be cooled. A reflective neutral density filter can be easier to apply since it does not absorb the heat, but the designer must attend to cooling the area where the reflected energy ends up so that this area does not overheat. Care must be taken if the energy is reflected back into the source since this reflected energy may overheat the lamp envelope resulting in sudden and destructive failure of the lamp.

It is possible to design a UVM without an image intensifier by using photodiode or pliotodiode/CCD hybrid cameras such as the 1024×1024 array camera designed by EG&G Reticon, or by using UV sensitive CCD arrays which have been coated with a UV phosphor such as lumigen or Unichrome. The disadvantage of a UVM without an image intensifier is that the UV levels at the samples must be much more intense which requires more powerful sources of UV light, creating more ozone in the lamp housing and greatly increasing the risk of potential damage to the sample. Therefore, it is presently contemplated that use of a UVM without an image intensifier is limited to short duration work in the UVC or to working on fixed, inorganic or light stable samples.

It is also possible to include more than one type of video system in the UVM. For example, it may be desirable to arrange light paths or camera changing sliders that allow UV image information to be sent to an image intensifier and camera while visible image information is sent to a color CCD camera, and NIR and IR image information is sent to a third IR array camera. In this way the final image formed by the computer system can cover an extraordinarily broad spectral range.

As image intensifiers can be damaged by exposure to light sources due to high photocurrent while in operation, it is desirable to design a system to shut down the power supply to the image intensifier if the current demand increases beyond a preset level. Once the tube is shut down, the current limit can be reset or the operator can choose to override it for a predetermined time period. The current limit on the image intensifier can be realized by sensing the nanoamp current consumption of the image intensifier during normal operation using a resistor and operational amplifier. The signal from the current sensing system can then be used to shut down the power supply for the image intensifier, or the light source 20 or both.

The UVM can be constructed with integral light feedback and dosimetry built in to monitor and stabilize the output of the source and integrate the exposure of selected areas of the sample. The light monitoring can be implemented through the video system or it can be accomplished with separate photodiodes using a small diverted portion of the illuminating light path typically just before the light enters the condenser. For advanced monitoring in living system work, it may be desirable to use a monochromator with a linear array detector to monitor not only the intensity of the illuminating wavelength but also the spectral characteristics. This monitoring version can be useful in supplying the feedback for synchronizing the video image capture with the illumination system.

The image information from the video camera is captured using an image capture board such as the Matrox Pulsar or the Matrox Genesis depending on the speed and level of capability desired for final imaging. A simple video capture system can be used to transfer the image information into digital form in the main memory of the computer where the computer controls the UVM and carries out the processing and display generation of the image data. A more sophisticated video processor such as the Genesis can be used in which the video processor carries out the image capture, data storage, data handling, mathematical processing and display generation, leaving the computer more time and resources to handle UVM control and supervision of the image processing tasks.

Image processing, includes overlay of several monochrome image planes to create a final multiplane color display. Typically color translation involves the conversion of three monochrome images from a non-visible region into the visible. The information in the monochrome images is overlaid to create the final color image with image planes displayed as red, green and blue information. As well as the image processor supplying overlay functions to form a full color translated image the processor also provides addition, subtraction, multiplication, logarithmic operations, boolean operations, dark offset and noise cancellation, contrast expansion and target tracking of image data. The image processor can also, in some cases, supply vector information on the movements of a sample or sample component to the supervising computer to direct the position drives of the UVM while following motion in the sample.

The image produced by the UVM can be generated by a video adapter such as a VGA or SVGA adapter included as part of the video processor or as part of the main computer. The final image is displayed on video monitor 300 which may be any type of video or graphics display monitor. While the control information can be displayed on the same video monitor 300 and the user can toggle back and forth between the image and the control screens it is most helpful to have two seperate displays one for video and one for control information so that both can be viewed at once.

The use of a separate adapter on the video processor is most desirable since then the first display 300 provides the final image while the second display 305 provides UVM control information and settings screens created using a program such as National Instruments Labview software to implement the UVM's graphic control panel.

The control system for the UVM consists of computer controlled power supplies to control the sources and the image intensifier; computer controlled positioning drives to control filter and focus drives; fine positioning drives to control the three dimensions of motion in the stage and condenser positioning systems; and environmental controls to keep the slide in the desired environmental conditions.

Figure 9:
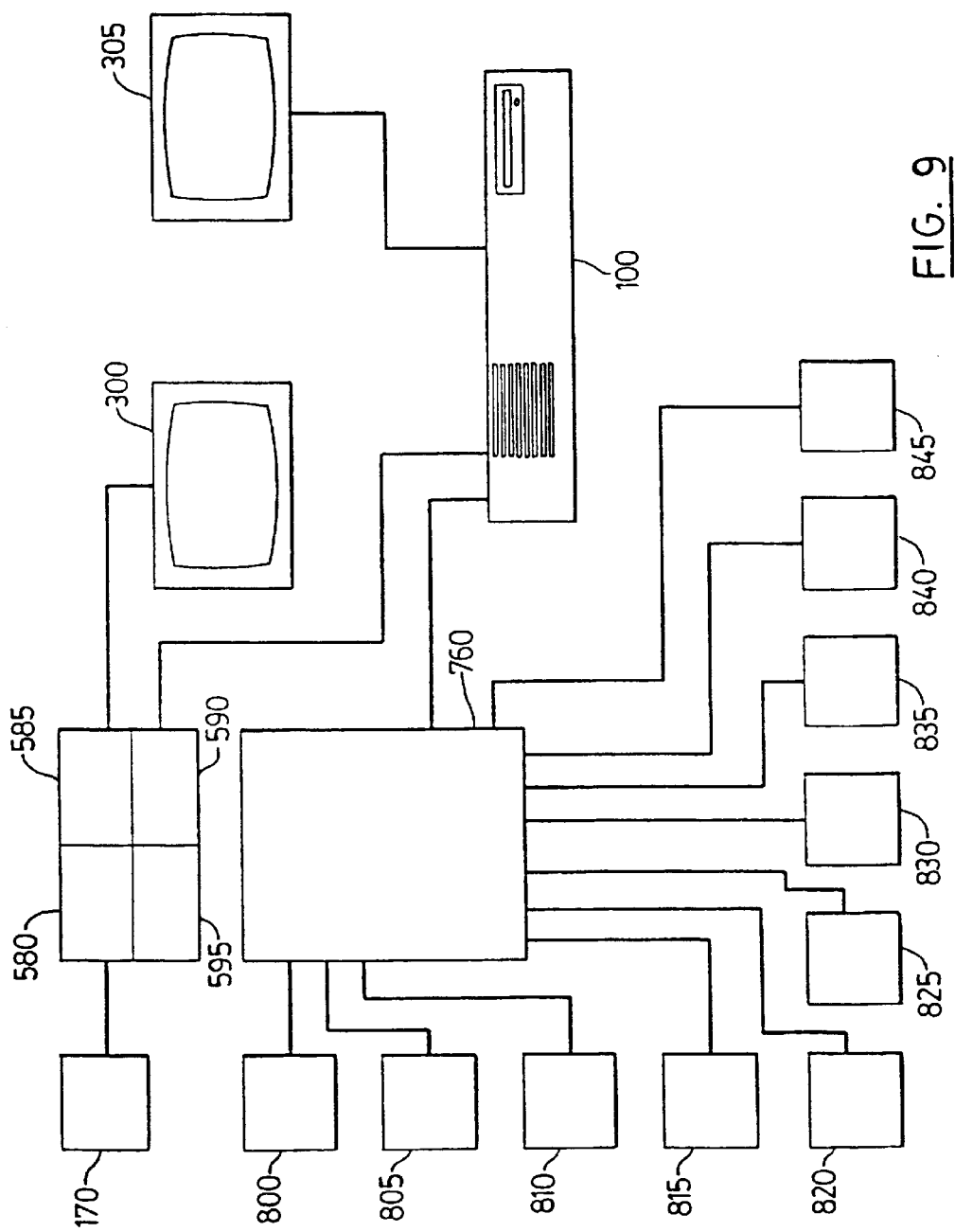
FIG. 9 shows a block diagram of the control and electronic functions of a color translating UV microscope in accordance with an embodiment of the present invention.

FIG. 9 shows the electronic signal path in one embodiment of the present invention. The video information is collected by video camera 170, and 190 and 195 if used, which can be a digital or analog camera consisting of a CCD array, a photodiode array, a tube camera or any other electronic image producing device. The image information is transferred to a video processor 580, 585, 595 and 590. This video processor can be internal to the computer in a form such as one or more of the Matrox Genesis video processor card, a combination of computer 100 processing and VGA or SVGA cards, or it can be an external subsystem. The video processor can perform several functions: converting the input signal to a digital format in processor section 580; performing mathematical functions, including image plane overlay or combinations, to form color images, addition, subtraction, dark offset or noise compensation, contrast enhancement, motion detection; three dimensional recreation from optical sections on the image data in a digital signal processor 595; creating a digital output display signal for driving a computer display monitor 300 in a display driver section 585 which can be an SVGA, RGB, NTSC, PAL, SECAM or other driver; and handling transfer of all or selected portions of the image data or control data to the computer 100 via section 590. The final image is displayed on display monitor 300 and the control information for the computer is displayed on display monitor 305. Alternately both the image and the computer control information can be alternately displayed on a single monitor 300 and selected under user control.

FIG. 9 also shows how the computer controls the various positions and modes of operation of the embodiment of the UVM depicted in FIG. 1. The control systems for the other embodiments described in this patent typically require more channels of control for the additional controllable components. The UVM is controlled via input/output drive controller 760 which both directs the control function and receives feedback from the movable component to indicate its current status. The intensity of the light source 20 and secondary light source 25 can be controlled via their power supplies 800, the monochromator center wavelength can be controlled by its drive system 805, the monochromator 50 bandwidth can be controlled by its drive system 810. The condenser 75 is controlled for X, Y and Z position by drive system 72 which is controlled by drive controller 815. The stage is controlled for X, Y and Z position by drive system 135 which is controlled by drive controller 820. The fine focus of the output screen of the image intensifier 160 onto the video camera 170 is controlled by Z drive system 165 which is controlled by drive controller 825. The gain of the image intensifier 160 is controlled by power supply 830. This leaves control ports 835, 840, and 845 to control other support functions such as reflected light operation switching via movable mirror 90 or focusing assist image switching via movable mirror 315 and temperature control of the stage via an eternally or internally attached stage heater. The computer 100 can also receive inputs from sensors in the UVM to provide information such as feedback on position and operating characteristics of the system or any other desired information to assist in any way including with image formation or sample control. These inputs are not shown in FIG. 9.

The control input screen would typically be implemented on the second display screen of the computer's two monitors whereas the first screen contains the image information. This second screen can show a virtual control panel with settings for all the controllable functions of the UVM. Using this system, the UVM operator will be able to see at a glance the settings and functions of the UVM. The settings of the UVM can be transferred back to the image system and displayed as part of the image information so that they are stored with the image for future reference and assistance in resetting the UVM to the correct operating parameters to reproduce a stored image.

The images produced by the UVM can be stored and transferred or transmitted in digital form on storage media such as optical storage, ZIP drive, SyQuest or other mass storage systems. Playback of the image information will only require a compatible video adapter, monitor and software. Alternately the images and the related data sets for the images can be communicated over the internet or other electronic data transfer means.

The basic version of the UVM includes: a quartz halogen lamp operated at high input energy to increase the UV output; a computer controlled motorized dual three-position filter wheel pair, with one filter wheel containing the three illumination light controlling filters, and the second filter wheel, containing 3 filters to limit the desired wavelengths and bandpasses of the image information, located between the objective lens and a UV sensitive video camera consisting of a lumigen coated CCD; a computer to control the filter rotation and receive filter position information; and a video capture system to supply the image information to the computer which then reconstructs the three sets of image information to create a final color translated image. This system uses standard microscope equipment for the supporting structure of the UVM and substitutes UV transmitting and reflecting materials for the optics of the microscope.

Another embodiment of this invention uses a special microscope slide in which a two (or more) bandpass filter is incorporated into the slide instead of the use of an illuminating monochromator or filter wheel. Use of this method requires only a suitable source and condenser on the illuminating side of the system for the production of a color translated image. All the filtering in this embodiment occurs between the objective lens and the image intensifier or camera. This system is believed to be particularly applicable for low cost specialized applications of the UVM in repetitive situations such as clinical labs or for retrofits of existing microscope designs.

Where filters are used in a rotating drive to perform the initial wavelength separation, or the secondary wavelength selection between the sample and the imaging device, then the filters can be driven by a stepper drive whose rotation steps are converted from the standard number of steps per rotation, such as eighteen steps per rotation, to a number which matches the number of filters used in the filter system. A six times speed increasing gear driven by an eighteen step motor would provide a filter drive with three steps per rotation which would be ideal for driving a three filter wheel at high rotational speeds. This acts as a method of obtaining high filter speed and of obtaining precise filter location after each step command.

The simpler embodiment of the present invention operates by converting differential optical absorption or other image information from an sample to differential colour information viewed by a user through an eyepiece or with a video system. As used herein, the term sample is intended to comprise biological, crystalline or other materials which have differential absorption or other image characteristics.

In a non-video system embodiment, an eyepiece looks through a rotating or otherwise cycling set of filters to provide an image of the output screen of an image intensifier. The image intensifier is employed to perform the dual functions of wavelength conversion, from whatever the sample spectra is to a broad visible spectra at the output, and to provide photon gain allowing the illumination required to be applied to the sample to be reduced. This later function allows the use of lower power illumination sources and a reduction in potentially harmful or influential energy at the sample. As will be apparent to those of skill in the art, the differential absorption wavelengths chosen can be broad bandpasses of wavelengths or narrow bandpasses or discrete monochromatic spectral lines or other spectral functions depending on the application.

A dual or triple set of coordinated filters is employed to resolve the black and broadband monochrome image from the image intensifier image into a coordinated multi-colour display by synchronously providing the desired wavelength of light to the image intensifier and filtering the output of the image intensifier. Typically, the output of the image intensifier is filtered for red, green and blue output using three filters, and this filter set is the third filter set from the lamp source, referred to herein as the image filter set. The second set of filters, referred to herein as the intermediate filter set, is located between the objective lens and the image intensifier. This filter set, and the use of the filters in it, is optional and depends upon the application. This filter set is intended to remove unwanted information from the light in the sample image, and these filters can isolate the transmitted light from fluorescent or Raman emissions or vice versa. It is contemplated that, in a further simplified embodiment of the present invention, these filters can provide all the spectral separation required for image formation and the third filter set can be eliminated.

The first filter set, referred to herein as the sample filter set, functions to separates the illuminating light into the desired spectral regions based on the differential absorption characteristics of the sample and the particular structures or components of the sample which are desired to be imaged.

Figure 10:
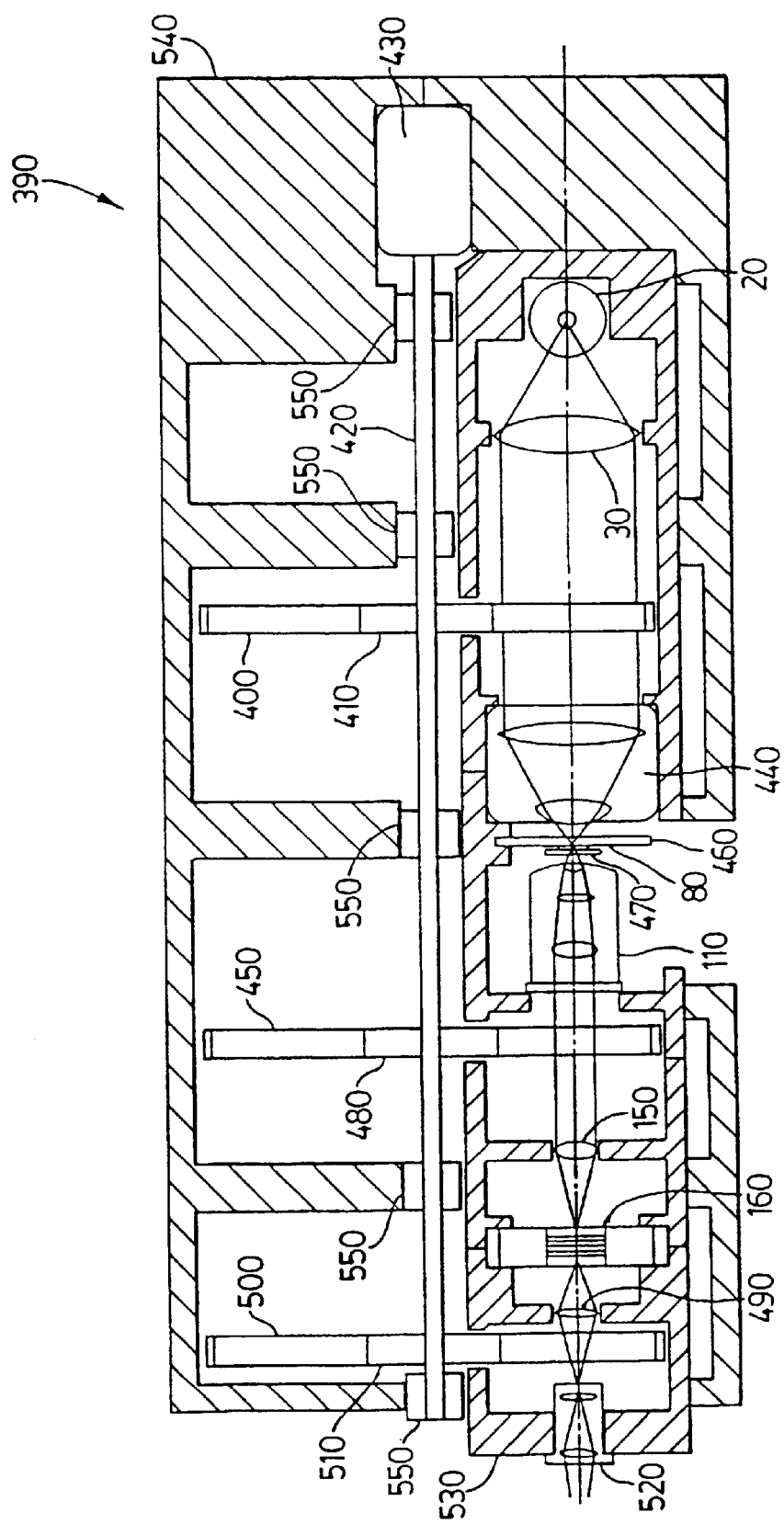
FIG. 10 shows a cross-sectional view of a microscope in accordance with an embodiment of the present invention.

FIG. 10 illustrates one embodiment of a simple version of the UVM. The light source 20 used in this embodiment of the present invention as the same as those in the previous embodiments. The light from light source 20 is collected into a substantially collimated beam by lense 30 and delivered to the sample filters 400 in the sample filter set 410 located in this case in a rotating filter wheel. FIG. 10 shows an embodiment of the simple version of the present invention. Filter wheel 410 and its related filters remove all but the desired wavelengths of light which is focused to a small point by the condenser 440.

The first filter set can be any combination of thin film interference filters or ionically or chemically dyed materials, or other suitable materials as will occur to those of skill in the art. The purpose of these filters is to choose the spectral regions that will define the image of the sample. Preferably, three wavelength regions are chosen which have very different spectral absorption characteristics for the sample, although more or fewer wavelength regions can be selected if desired. An example of a three filter set of interest can include three hundred and sixty five, two hundred and seventy and two hundred and fifty six nanometer bandpass filters for looking at living cells.

In a preferred aspect, one or more pre-filters can be added between the source and the sample filter wheel or between the sample filter wheel and the condenser. A pre-filter which cuts off all but the longest wavelength in the filter set, for example the three hundred and sixty five nanometer wavelength in the example above, can be used for searching and focusing since it has a reduced potential of inducing cellular damage than the two shorter wavelengths. As will be apparent, when this pre-filter is in place the microscope operates in monochrome mode. When the desired field of view is found and once the image is in focus, the pre-filter is removed allowing the system to operate in full colour mode. As an alternative, the sample filter set can include a filter which has a dual bandpass, one in the visible light range and one in the UV light range. A selectable pre-filter pair then selects either the visible or UV component from this filter by providing a long pass or short pass filter function.

Another embodiment of the present invention employs a monochromator with the output spectral bandwidth selected by a circular or linear aperture and the wavelength selected by a scanning, vibrating or rotating mirror or the like which is synchronized with the intermediate and image filter sets. This has the advantage of making the choice of wavelengths continuously variable and the bandwidths independently variable. It is presently believed that this system lends itself well to spectral imaging, spectrally scanning or microspectroradiometric imaging.

Another embodiment of the present invention employs a special microscope slide in which a two or more bandpass filter is incorporated into the slide to remove the need for an sample filter wheel. Using this method means that only a suitable source and condenser are required on the illuminating side of the system for the production of a colour translated image. All the filtering in this embodiment occurs between the objective lens and the user. This system is presently believed to be particularly applicable for retrofits of existing microscope designs.

In the present invention, the condenser must be able to transmit UV and visible light and, for some applications, must also be able to transmit infrared light. Reflective or refractive condensers can be employed and brightfeld, darkfield, phase contrast or other versions can be employed as required. For deep UV or vacuum UV use, deuterium sources or metallic spark sources can be combined with metallic thin film interference filters and entirely or partially reflective optics or lithium fluoride optics to provide the light to the sample. For vacuum UV operation, it is contemplated that the areas of the light path from the source to the image intensifier in the microscope must be operated in a vacuum or purged with dry nitrogen since oxygen substantially absorbs UV light below one hundred and ninety five nanometers. The condenser 440 illuminates the sample 80 which is mounted on slide 460 and protected by cover slip 470.

The sample 80 can be mounted on slides and contained with cover slips, if necessary, which are transparent to the wavelengths employed in the system and quartz and sapphire are suitable materials for UV work. As will be apparent to those of skill in the art, for some applications no cover slip may be required. The sample mountant, lens adhesives and immersion fluid for immersion lenses must also be taken into account to make sure that they do not fluoresce or absorb in the wavelength regions being employed. Glycerin and distilled water are suitable materials for use as the slide mountant and as the optical immersion fluid. Lenses typically must be gas spaced, optically contacted or cemented using a suitable substantially UV transparent optical adhesive.

The light transmitted by the sample or emitted through fluorescence or Raman processes is focused by, the objective 110. The objective may be a conventional fixed tube length design in which case tube lens 150 is not required. As will be apparent, the objective lens must have the same capabilities as in the previous embodiments in that it must be capable of utilising the wavelengths of light employed in the system.

The tube lens 150 is used with infinity corrected objectives. The light from the objective passes through intermediate filter 450 or one of the other several filters contained in the intermediate filter wheel 480. These filters select the transmitted light information or the autofluorescent information or the Raman information in the sample image prior to this light information reaching the image intensifier. The tube lens 150, or the objective 110 in a non ICS system, focuses the image of the sample on the input window of the image intensifier 160.

The second or intermediate filter set is used to isolate components of the light transmitted by, or originating from the sample. It is common for biological materials to exhibit broadband blue autofluorescence when illuminated by a short wave UV light source 20. This autofluorescence can be strong enough to fog the desired UV image. It is therefore important to remove the blue autofluorescence from the image prior to it encountering the image intensifier. The UV image can be isolated from the autofluorescent image by employing a UV transmitting and visible absorbing or reflecting filter between the objective and the image intensifier.

Alternatively, it can be desirable to study the fluorescent or autofluorescent components of the light emitted by the sample due to internal chemical components of the sample or due to fluorochromes added to the sample. This can be accomplished with filters which transmit the wavelengths of the fluorescence or autofluorescence and block the exciting UV wavelengths. It is also contemplated that narrow band notch rejection filters can be employed to observe the Raman re-emission wavelengths from the sample. As will be apparent to those of skill in the art, the Raman notch filter attenuates the narrow band exciting wavelength in order to allow the Raman emissions to be viewed at wavelengths other than the exciting wavelength.

The light from the output window of the image intensifier 160 is relayed to the eyepiece by the relay lens 490. The light from the image intensifier output is filtered by filter 500 or one of the other several filters contained in the image filter wheel 510. This filter wheel provides the differential colour separation of the broadband emission of the output phosphor of the image intensifier thus completing the colour translation process. The colour translated image is viewed through the eyepiece 520 by either an observer or a photographic or CCD camera or other imaging means.

The image intensifier fulfills three functions in the present embodiment of the invention. First, it converts light within the spectral sensitivity range of the photocathode to light of spectra determined by the phosphor used on the output screen. This conversion is used to convert UV or IR light into visible light. Second, it provides photon gain between the input and output of the microscope, allowing reduced amounts of light to be used to form the image of the sample. This means that the sample is exposed to less light than in a normal microscope and it is contemplated that this is particularly important in UV microscopy as UV light in the regions below 380 nanometers can have strongly detrimental effects on biological samples. The use of the image intensifier tube reduces this exposure to values typically $\frac{1}{10,000}$ of the intensity which can otherwise be required to form an image.

The third function of the image intensifier is to convert narrow spectral input photons into broadband output light so that the filter based colour conversion process can operate.

The image intensifier employed is not particularly limited and can be a proximity focused diode design or a single or double microchannel plate design or any other suitable type of image intensifier. It is presently contemplated that the double microchannel plate offers the highest photon gain, but at the expense of resolution and signal to noise ratio. The double microchannel plate and high operating voltage are preferred when the least possible interference with the normal activities of a biological sample is desired.

The choice of an appropriate input photocathode for the image intensifier is important to the proper operation of the filter, but the necessary considerations will be apparent to those of skill in the art. For example, short wave UV conversion requires a photocathode that is sensitive in the deep UV, such as the S20 photocathode. Visible or extended red operation, for fluorescent, autofluorescent or Raman imaging, requires the addition of different materials to the photocathode. Visible insensitive image intensifiers, commonly described as solar blind, provide UV images without the interference from visible autofluorescence from the sample. In general, a good choice of photocathode is one which exhibits wide spectral bandwidth and high sensitivity.

Image intensifiers generally use high efficiency output phosphors which have narrow spectral emission bandwidths, typical examples are P20 or P11 phosphors. For the color translation process, the output phosphor must provide blue, green and red light to supply the blue, green and red image information. Suitable phosphors for this application are the P43 phosphor, or any of the phosphors commonly used for monochrome television display screens, or alternatively, a mixture of red, green and blue phosphors normally used in colour television display screens can be mixed and used for the output screen of the image intensifier.

The third filter set, the image filter set, selects the desired spectral range of the image intensifier output synchronously with the wavelengths supplied to the image intensifier input by the sample and intermediate filters it is contemplated that this filter set will typically comprise blue, green and red filters chosen for transmission and bandpass functions so that the sum of the output of the three filters output from the image intensifier is perceived as white light by the eye of the user or by a colour CCD camera.

For the most accurate image formation, a correcting optical system should be applied to correct for the differing indices of refraction of this filter set and the intermediate filter set so that the focal plane of the image is the same for all filters. In the same way, these two filter sets should have matched thickness to prevent the introduction of aberrations in the image due to unmatched path lengths. Infinity corrected optical systems greatly reduce the image variance from filter to filter.

Depending on the desired application, other colour combinations can be employed to give a more accurate or enhanced view of the sample wavelengths being employed. In other words, filters can be selected which more accurately portray the spectral bandwidths and ratios of the filters in the sample and intermediate filter sets it is contemplated that this can provide potentially important information on harmonic relationships in light energy in biological and crystal samples.

As the output of the image intensifier is a phosphor screen, it represents a lambertian source and light from this screen must be transferred or relayed to the observer or colour CCD camera. This relay can be accomplished in a variety of manners, including a short tube microscope consisting of a microscope eyepiece and a relay lens, or with a fiber optic relay bundle or taper, commonly known as a minifier.

Since the image intensifier intercepts the image from the sample, UV light from the source cannot normally pass through to the observer from the sample and the eyepiece does not have to filter all the UV from the image. Careful analysis of the spectral emission from the image intensifier phosphor and effective filtering of any unwanted wavelengths will enhance the contrast ratio and the apparent focus of the final image. The eyepiece can be a monocular, binocular or trinocular system commonly used in light microscopes or any other viewing arranged such as would be obvious to one skilled in the art of microscopy.

It is presently contemplated that this embodiment of the invention can also be employed with a standard microscope stand design and can be retrofitted to existing microscopes. However the high resolution possible, due to the use of ultraviolet light, places increased demand on the microscope stand to eliminate vibrations.

In a preferred embodiment of the present embodiment of the invention, a tubular design is employed wherein the imaging optics are mounted in a common tubular frame with the stage and illuminating optics. As in preceeding examples this design renders the optical system less susceptible to external vibration as the whole system will vibrate in substantially the same way and the vibrations will therefore be common and in phase for all of the components which are critical to forming a good image.

If a rotary or oscillating filter drive is employed, it is preferred to mount the drive outside and not in direct contact with the tubular frame of the imaging components of the microscope. In this case, the drive components are mounted in a second outer tube which also supports the inner tube on vibration damping mounts. The rotating filters project into the inner imaging tubes through slots in the tube wall and do not come into direct contact with the inner tube at any point. The outer tube also serves as a light and dust-tight housing to keep stray light and dust from contaminating the image or the components in the imaging tube. The imaging, illuminating and object supporting components are all mounted in a common tubular housing 530 in order to reduce vibration which deteriorates the image. This housing is referred to as the inner or imaging housing. The entire instrument is contained in an outer tube 540 which serves as a light and dust tight enclose, provides electrical and magnetic shielding, and serves as the mounting frame for the rotating components. The inner and outer housings are isolated from each other by antivibration mounts. The rotating filter wheels 410, 480, and 500 are mounted on a common shaft 420 which is placed in rotary motion by the motor 430. The shaft 420 is supported by bearings 550 which are isolated from the inner microscope tube 530 by gaps or antivibration mounts located in the gaps.

It is presently contemplated that the most effective means of synchronizing the two, or three, filter sets used in this invention is to mount the filter sets in rotating filter wheels that are mounted on a common shaft and driven by a single driving motor. The driving motor can be a DC motor with variable speed and synchronization or it can be a stepper motor or a synchronous motor or a servo motor. Where the reduction of magnetic and electrical fields is a concern, the driving motor can be an air or hydraulic motor. For some applications, the motor drive or drives may need to be synchronized to the scan frequency of a CCD or other type of video camera. In any event, the filters will maintain phase position and speed with respect to each other.

Alternatively, the filter wheels can be operated by two or three independent but electronically coordinated synchronous motors, stepper motors or other electronically controllable and indexable rotating means.

Another embodiment of the present invention employs an oscillatory or resonant vibrating system to move the filters into the proper location. This embodiment employs a mechanical oscillator or vibrator to move the filters into the appropriate light paths, but this is not presently a preferred method due to the possibility of the introduction of vibration into the system.

A further embodiment of the present invention employs scanning, oscillating and/or revolving mirrors to direct the light paths through the appropriate filters. This embodiment has the advantage of a reduced moving inertia and consequent reduced vibration. As will be apparent, the filters in this system do not move and only the light path changes with the angle of the mirror system.

The choice of the speed for filters passing image is determined by the application. For example, the use of this system for direct visual viewing through an eyepiece can be effective with rotating filter speeds of one filter set cycle twenty to thirty times per second. This implies a rotation speed for a three filter set of thirty to sixty revolutions per second which equals a rotation speed of one thousand and eight hundred rpm. For use with a CCD camera, it is desirable to synchronize the rotations with the frame rate of the CCD. It may also be desirable to have a rotational speed for the filter wheel which provides a full cycle of the filters in each video frame.

It is contemplated that a substantial benefit of the present invention is that it allows the observer to view the sample in real time without requiring computer processing or image reconstruction. This is particularly applicable to the observation of living biological systems including cells, intra and intercellular components, bacteria, viruses, parasites and other dynamic components or processes.

It is important to choose the output phosphor of the image intensifier with due consideration of the required response speed of the phosphor. The decay time of the phosphor must be sufficiently short that the image from a previous colour does not persist into the time interval for the following colour. In order to provide stop motion effects for freezing the motion of a rapidly moving sample either the image intensifier can be gated at precise intervals by external electronics or the illuminating light path can be shuttered by a controllable shutter again at precisely controlled intervals by external electronics. The shuttering can also be used for dose reduction or selective wavelength elimination for dose reduction on the basis of relative harmful effects of various doses. For instance the illuminating shutter may be opened only twice per second during the least harmful wavelength of a single wavelength interval while the microscope was being used for searching, once the desired sample was located then the full range of wavelengths is allowed to pass by the scanner.

Further, neutral density filters can be introduced into the illuminating beam path during searching or long term tracking of components to reduce the exposure of the sample. The neutral density filter is chosen to provide an image only slightly above perception limit of the observer's eye or above the noise floor of the CCD. Once an sample of interest is located the filter is removed allowing the image intensity to take more complete advantage of the available dynamic range of the observer's eye or the CCD.

The stage employed with the present invention can be a conventional stage, however for the very high resolution which the present invention is capable, the stage will preferably be of the nanopositioning type.

Polarizing means in the form of polarizing sheet film or of any of the prismatic polarizer which can transmit and effectively polarize the light in the illuminating beam can be used in either or both of the illuminating path between the source and the sample or in the path between the objective and the image intensifier to give polarization and rotary information on the optical rotary power of the sample. These polarizing means can be fixed or can be rotating or vibrating in one of the sample or intermediate filter sets or they can be rotating in their own filter sets synchronized with the other filter sets.

Figure 11:
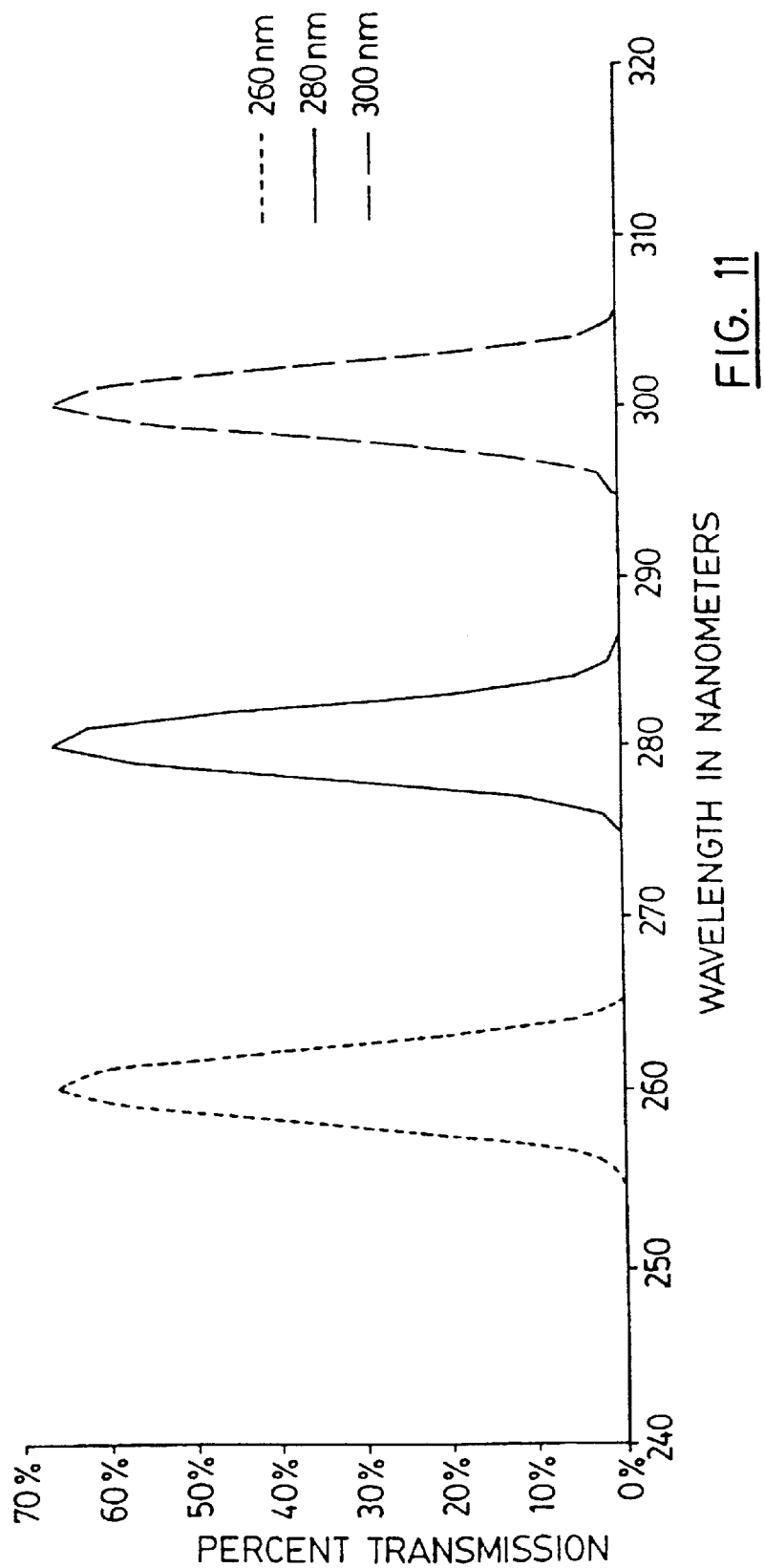
FIG. 11 shows a graph of a typical UV illumination filter spectra.

FIG. 11 shows three typical bandpass filters which can be used in the object filter wheel. In this illustration, the filters are narrow bandpass filters at 260, 280 and 300 nanometers. The relative transmission peaks of the three filters are shown to be equal in this illustration but they can be made unequal in order to compensate for different spectral energies available from the source. For instance when the source was deficient in energy at two hundred and sixty nanometers then the two hundred and sixty nanometer filter can have a higher peak transmission than the other two filters.

FIG. 12 shows three typical bandpass filter which can be used in the image filter wheel. This illustration shows blue, green and red bandpass filters centered at four hundred and fifty, five hundred and twenty five and six hundred and fifty nanometers respectively. The location of the center wavelength, the bandpass function and the relative peak transmissions of these three filters can be varied to match the spectral output of the phosphor in the image intensifier output screen and to provide the desired colour information in the viewed image.

Figure 14:
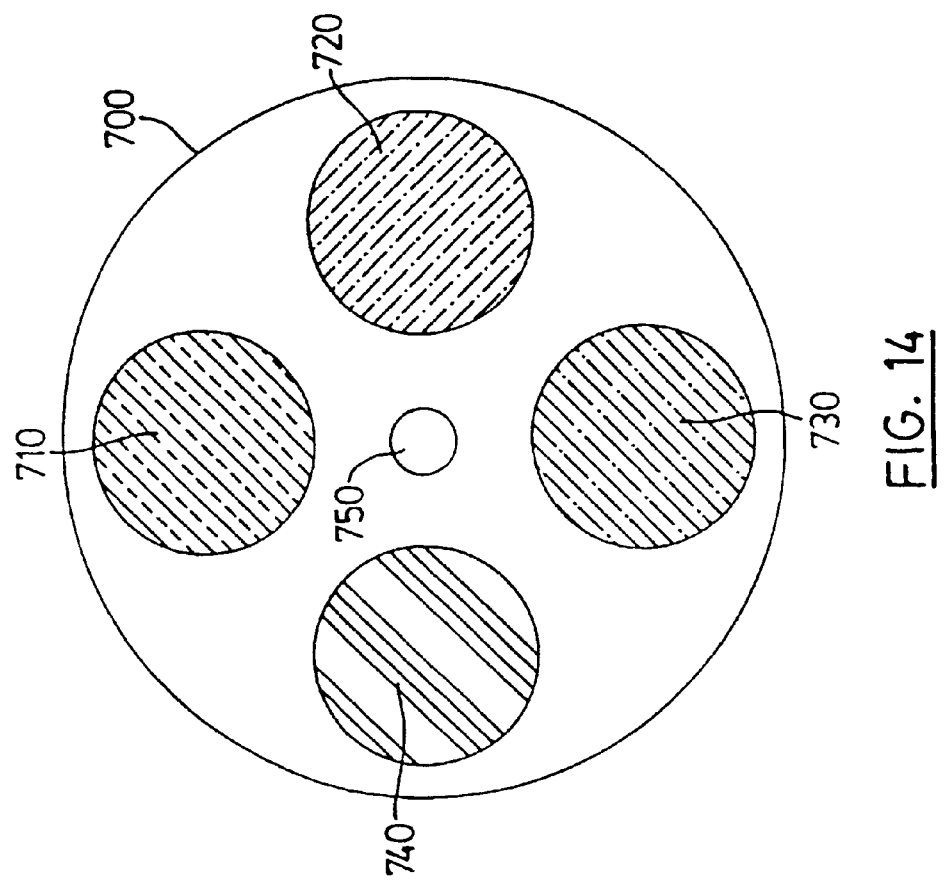
FIG. 14 shows a four-filter filter wheel which can also be employed with the microscope of FIGS. 2, 7, and 10.
Figure 13:
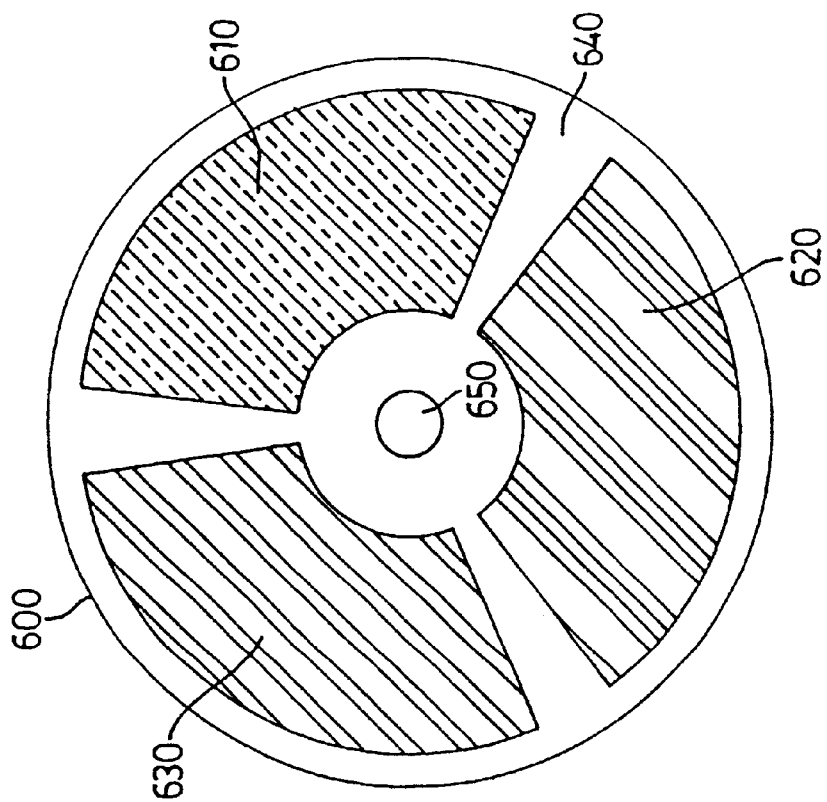
FIG. 13 shows a three-filter filter wheel which can be employed with the microscope of FIGS. 2, 7, and 10.

FIGS. 13 and 14 show two typical filter wheels that can be used in embodiments of the present invention. In FIG. 13, the wheel is a three sector wheel 600. The sector shape of the filter 610, 620, and 630 allows the maximum light exposure time with minimum dark times between filters. The width of the supporting struts 640 sets the dark interval between the different filters. It can be important to coordinate the width of the strut 640 in the sample filter wheel, and in some cases in the intermediate filter wheel, with the decay time of the image intensifier. The filter wheel is driven by a shaft fixed to the wheel and shown as 650.

FIG. 14 shows a four filter wheel 700 in which standard circular filters are used as opposed the non-standard shaped sector filters in the previous example. The filters shown as 710, 720, 730, and 740 are mounted in the wheel 710 and driven by a shaft fixed to the wheel and shown as 750.

Modes of Operation: The final image in the UVM is created by combining two or more images which are collected under different conditions of illumination angle, wavelength, bandwidth, polarity, phase or intensity. In the table of Appendix A, three illumination schemes are repetitively cycled along with a corresponding set of image filters to produce three images which are combined numerically by a computer to produce the final image.

Appendix A comprises a non-comprehensive table listing some of the many modes of image creation which are possible with a UVM system in accordance with the present invention. A conventional microscope normally operates in one mode at a time. Changing modes requires changing filters, optics, sources or cameras. As the UVM of the present invention is designed to switch modes rapidly under computer control, and ideally rapidly enough that modes can be switched several times per second in order to accomplish real time microscopy of dynamic samples, the microscopist gains the ability to mathematically convolve information from the various modes to produce highly informative final color images. These images provide chemical and biochemical spectrophotometric, optical activity, and optical characteristics, as well as spatial information in the same final image.

In this table, illuminating light with wavelength 1 in nanometers which has a bandpass (BP) shown in nanometers is directed at the sample from the described angle. The resulting image is filtered by the image filter (ifilter) and intensified by the image intensifier operating at a typical gain shown (igain) to produce an image in one of three image planes (A, B and C). These image planes are combined by the computer processing system to yield the red, green and blue information in the final color image displayed on the image video display monitor of the UVM system. In the red, green and blue image columns of the table, an image plane designation preceded by the negative sign where both the designator and the negative sign are contained inside a bracket denotes taking the negative image of that image plane. For example, (−B) means to take the negative image of the information on the B image plane. These are only some of the many contemplated modes of operation that the fully implemented UVM makes available.

One particular embodiment of a color translating UV microscope (UVM) is described with reference to FIG. 2 and FIG. 3. In this embodiment, the light from a quartz halogen lamp 20, is focussed into a collimated beam by a visible and NIR light transmitting lens 30. Light from a deuterium arc lamp 25 is focused through a UV transmitting lens 35 into a second collimated beam. The two collimated beams are combined in the beam combining prism or mirror system 40. The mirror system 40 can be under the control of computer 100. The combined beam now containing UV, visible and NIR light is filtered by filter 45 to remove unwanted spectral energy, typically long wave NIR and IR. Specific bandwidths or relatively monochromatic regions of the incoming light are then selected by the monochromator system 50. Alternatively, appropriate filters (or optical mechanisms) can be utilized to further select for plane-polarized light of a selected or broad bandwidth. The wavelength, slit or iris bandwidth, and grating are selected under control of computer 100. The light from the monochromator is reflected by mirror 60 which transfers the light to mirror 65. Mirrors 60 or 65 can be coated with special reflective coatings to further filter or selectively reflect the desired wavelengths of light. The light is then focused on the sample by condenser 75. Condenser 75 is focussed in the X, Y and Z directions by a drive system 135 (FIG. 3) under the control of computer 100. The sample is supported by a stage 130 which is positioned in the X, Y and Z directions by the drive system 135 under the control of computer 100. The light from the sample is focussed by objective lens 110 which can be a fixed focal length or infinity corrected type of objective as shown in this drawing. The light from the objective passes through filter 85 (FIG. 2) which can be a shortpass, bandpass, longpass or Raman notch rejection filter or a combination of the above filters with a polarizer. The filtered light is imaged onto the input screen of the image intensifier 160 by the tube lens 150 in the infinity corrected version of the system. The image intensifier both amplifies the light signal and converts it to a visible output. The light emitted by the output phosphor screen of the image intensifier is relayed by relay lens 180 to form an image on the surface of the video camera 170 which can be a photodiode array camera, a CCD camera or a tube video camera 170 or any other type of electronic or digital imaging device. The video camera is adjusted for focus by the Z direction positioning drive 350 under computer control. The signal from the video camera 170 is converted to digital information in computer 100, processed by the computer and displayed on the digital or video monitor 300. The control, operational and position information is displayed on the computer monitor 305. The entire microscope optical system is contained in a tubular design, the tube being the supporting tube in which all the other image forming components are mounted.

The above-described embodiments of the invention are intended to be examples of the present invention and alterations and modifications may be effected thereto, by those of skill in the art, without departing from the scope of the invention which is defined solely by the claims appended hereto.

APPENDIX "A"
Examples of Imaging Modes for UVM

| MODE | image plane one (A) | | | | | image plane two (B) | | | | |
|---|---|---|---|---|---|---|---|---|---|---|
| | λ | BP | angle | ii gain | i filter | λ | BP | angle | ii gain | i filter |
| 1 | 250 | 10 | BF | 10 | 300 SP | 270 | 10 | BF | 10 | 300 SP |
| 2 | 250 | 10 | BF | 10 | 300 SP | 270 | 10 | BF | 10 | 300 SP |
| 3 | 250 | 10 | RF | 10 | 300 SP | 270 | 10 | RF | 10 | 300 SP |
| 4 | 250 | 10 | DF | 100 | 300 SP | 270 | 10 | DF | 100 | 300 SP |
| 6 | 300 | 100 | DF | 100 | 365–450 | 300 | 100 | DF | 100 | 450–575 |
| 7 | 300 | 100 | DF | 10 | 250–260 | N | | | 1000 | 360–555 |
| 8 | 250 | 50 | BF | 10 | 300 SP | 250 | 50 | BF | 100 | 300 LP |
| 9 | 350 | 50 | BF | 100 | 380–480 | 350 | 50 | BF | 100 | 480–530 |
| 10 | 255 | 5 | BF | 50 | 250–260 | 265 | 5 | BF | 50 | 260–270 |
| 11 | 255 | 5 | BF | 50 | 250–260 | 265 | 5 | BF | 50 | 260–270 |
| 12 | 450 | 10 | DF | 100 | 440–460 | 550 | 10 | DF | 100 | 540–550 |
| 13 | 450 | 10 | DF | 100 | 440–460 | 550 | 10 | DF | 100 | 540–550 |
| 14 | 250 | 2 | BF | 1000 | 248–252N | 300 | 2 | BF | 1000 | 398–402N |
| 15 | 250 | 2 | BF | 1000 | 248–252N | 300 | 2 | BF | 1000 | 398–402N |
| 16 | 250 | 2 | BF | 1000 | 248–252N | 300 | 2 | BF | 1000 | 398–402N |
| 17 | 250 | 2 | BF | 1000 | 248–252N | 500 | 2 | BF | 1000 | 498–502N |
| 18 | 250 | 2 | BF | 1000 | 248–252N | 500 | 2 | BF | 1000 | 498–502N |
| 19 | 300 | 10 | BF | 10 | 350 SP | 300 | 10 | RF | 10 | 350 SP |
| 20 | 400 | 20 | BF | 1000 | 190–210 | 600 | 20 | BF | 1000 | 290–310 |

| MODE | image plane three (C) | | | | | red image | green image | blue image | DESCRIPTION |
|---|---|---|---|---|---|---|---|---|---|
| | λ | BP angle | ii gain | i filter | | | | | |
| 1 | 290 | 10 BF | 10 | 300 SP | | A | B | C | UV TRANSMITTED |
| 2 | 290 | 10 BF | 10 | 300 SP | | C | B | A | UV TRANS. REVERSED |
| 3 | 290 | 10 RF | 10 | 300 SP | | A | B | C | UV REFLECTED |
| 4 | 290 | 10 DF | 100 | 300 SP | | A | B | C | UV DARK FIELD |
| 6 | 300 | 100 DF | 100 | 575–800 | | A | B | C | UVB/C AUTOLUMINESCENT |
| 7 | N | | 1000 | 555–700 | | A | B | C | UV PHOSPHORESCENCE |
| 8 | 550 | 200 DF | 10 | 450–650 | | A | B | C | UV/DARKFIELD MIXED |
| 9 | 350 | 50 DF | 100 | 530–700 | | A | B | C | UVA AUTOLUMINESCENT |
| 10 | 275 | 5 BF | 50 | 270–280 | | A | B | C | UV SPECTROCHEMICAL |
| 11 | 275 | 5 BF | 50 | 270–280 | | B | B − A | B − C | UV DIFFERENTIAL |
| 12 | 650 | 10 DF | 100 | 640–660 | | A | B | C | VISIBLE SPECTROCHEMICAL |
| 13 | 650 | 10 DF | 100 | 640–660 | | B − A | B − C | A + B + C | VISIBLE DIFFERENTIAL |
| 14 | 350 | 2 BF | 1000 | 348–352N | | A | B | C | UV RAMAN |
| 15 | 350 | 2 BF | 1000 | 348–352N | | B − A | B | B − C | UV RAMAN DIFFERENTIAL |
| 16 | 250 | 10 DF | 100 | 270 SP | | A | B | C | UV RAMAN OVERLAY |
| 17 | 900 | 2 BF | 1000 | 898–902N | | A | B | C | UV-VIS-NIR RAMAN |
| 18 | 900 | 2 BF | 1000 | 898–902N | | B − A | B | B − C | UV-VIS-NIR RAMAN DIFF. |
| 19 | 300 | 10 DF | 10 | 350 SP | | (−A) | B | C | BF RF DF COMPARISON |
| 20 | 1000 | 20 BF | 1000 | 490–510 | | A | B | C | UV-VIS-NIR HARMONIC |

λ = wavelength, N = none, BP = bandpass, SP = shortpass, LP = longpass, BF = brightfield, RF = reflected, DF = darkfield, SU = slit ultramicroscopic, wavelengths in nanometers

I claim:

1. A method of producing an observable image representing the differential absorption of light by a sample, the method comprising:
   a) illuminating the sample with non-visible light;
   b) receiving light from the sample as an image of the sample and converting said light image to a visible polychromatic light image; and
   c) selecting a color from said polychromatic light image to thereby generate said observable image.

2. A method according to claim 1, wherein said illuminating light is ultra-violet light or infra-red light.

3. A method according to claim 2, wherein said illuminating light has a wavelength or wavelengths selected from a group of n pre-selected wavelengths or wavelength regions, n>1.

4. A method according to claim 3, wherein said color is selected from a group of n pre-selected colors, n>1.

5. A method according to claim 4, including synchronously changing the wavelength(s) of said illuminating light and said selected color.

6. A method according to claim 5, where the conversion of said light image to said polychromatic light image is carried out by a photon gain device.

7. A method according to claim 1, including synchronously changing the wavelength(s) of said illuminating light and said selected color.

8. A method according to claim 1, where the conversion of the light image to the polychromatic light image is carried out by a photon gain device.

9. A method of producing an observable image representing the differential absorption of light by a sample, the method comprising:
   a) illuminating the sample with light of a first selected wavelength or wavelength region;
   b) receiving light from the sample as an image of the sample and converting said light image to a polychromatic light image; and
   c) selecting a pre-determined wavelength or wavelength region from said polychromatic light image to thereby generate said observable image.

10. A method of producing a visible image representing the differential absorption of light by a sample, the method comprising:
   a) illuminating the sample with non-visible light, the wavelength or wavelength region of the illuminating light being cyclically selected from a pre-determined group of wavelengths or wavelength regions;
   b) receiving light from the sample as an image of the sample and converting said light image to a polychromatic light image;
   c) filtering said polychromatic light image to thereby obtain a wavelength or wavelength region therefrom for display as said visible image, the displayable light being cyclically selected from a pre-determined group of wavelengths or wavelength regions; and
   d) periodically and synchronously changing the wavelengths or wavelength regions of the illuminating light and the displayable light.

11. A method according to claim 10, wherein said period is sufficiently short so as to integrate displayable light of different wavelengths or wavelength regions to the human eye.

12. An apparatus for producing an observable image representing the differential absorption of light by a sample, the apparatus comprising:
   a) means for illuminating the sample with non-visible light;
   b) means for converting light received from the sample as an image thereof to a polychromatic light image; and
   c) means for selecting a color from said polychromatic light image to thereby generate said observable image.

13. A microscope for translating spectral information to a visible color image, comprising:
   a light source providing light substantially not visible to the human eye;
   a stage for holding a sample;
   a first set of at least two filters for separating light from the light source into spectral components;
   a lens system for illuminating the sample with light emanating from the first filter set;
   means for converting light received from the sample to visible polychromatic light;
   a second set of at least two filters for separating the visible polychromatic light into color planes;
   wherein the first and second filter sets are synchronized with each other so as to enable the color planes to be recombined into a visible multicolor image.

14. A microscope according to claim 13, wherein the first and second filter sets are each located on wheels mounted to a common shaft.

15. A microscope according to claim 13, wherein the light conversion means comprises an image intensifier for converting images outside the normal range of human vision to images inside the range of human vision.

16. A microscope according to claim 15, wherein the image intensifier reduces the exposure of the sample being imaged in order to reduce effects on or damage to the sample.

17. A, microscope according to claim 16, wherein the image intensifier converts narrow spectral inputs to broadband spectral outputs to allow filter based color translation.

18. A microscope according to claim 15, wherein one or more of said filters have spectral responses engineered to compensate for differences in at least one of:
   a) the intensity of illuminating spectra from the source;
   b) differences in the spectral transmission efficiency of optical components employed in the lens system;
   c) differences in the spectral photon to electron conversion efficiency of a photocathode of the image intensifier; and
   d) differences in the spectral output of the image intensifier.

19. A microscope according to claim 13, including an intermediate set of at least one filter disposed so as pass from the sample only the wavelength(s) of the illuminating light.

20. A microscope according to claim 19, wherein the intermediate filter set is synchronized with the first filter set.

21. A microscope according to claim 13, including an intermediate set of at least one filter disposed to reject from the sample only the wavelength(s) of the illuminating light, thereby aiding fluorescent or autofluorescent imaging.

22. A microscope according to claim 21, wherein the intermediate filter set is synchronized with the first and second filter sets.

23. A microscope according to claim 13, including an intermediate synchronized set of at least one narrowband filter arranged to reject from the sample only the wavelength(s) of the illuminating light in order to enable any Raman re-emission spectra to be viewed.

24. A microscope according to claim 13, including polarizing means capable of transmitting the wavelength(s) being used for illumination, said polarizing means being located in at least one of first and second positions, the first position being between the light source and the sample, the second position being between the sample and the conversion means.

25. A microscope according to claim 24, wherein the first and second sets of filters are disposed on wheels mounted to a common shaft, the polarizing means being disposed on a wheel mounted to the common shaft in synchronicity with the first and second filter wheels.

26. A microscope according to claim 13, including a tubular support means for reducing vibration.

27. A method of producing an image representing the differential absorption of light by a sample, comprising:
   a) illuminating a sample with light of a first desired wavelength(s) by imposing a first filter between a multi-wavelength source and the sample;
   b) receiving light from the sample at a photon gain device which converts the received light to an intensified white light;
   c) filtering the intensified white light with a second filter to obtain visible light at a pre-selected wavelength(s) for said desired wavelength;

d) forming an image from said filtered intensified white light; and e) synchronously changing the first and second filters and repeating steps (a) through (d) to illuminate the sample with light of a second desired wavelength and form an image from visible light obtained from the intensified white light at a second pre-selected wavelength for said second desired wavelength.

* * * * *

UNITED STATES PATENT AND TRADEMARK OFFICE
CERTIFICATE OF CORRECTION

PATENT NO. : 6,650,357 B1
DATED : November 18, 2003
INVENTOR(S) : Timothy M. Richardson It is certified that error appears in the above-identified patent and that said Letters Patent is hereby corrected as shown below:

<u>Title page,</u>
Item [73], Assignee, delete "Richardson Technologies, Inc., Ontario (CA)" and replace with -- Northern Edge Associates Inc., Ontario Canada --

Signed and Sealed this

Twenty-eighth Day of June, 2005

JON W. DUDAS
*Director of the United States Patent and Trademark Office*